US009725506B2

(12) United States Patent
Dillon et al.

(10) Patent No.: US 9,725,506 B2
(45) Date of Patent: Aug. 8, 2017

(54) LEVELS OF BCMA PROTEIN EXPRESSION ON B CELLS AND USE IN METHODS OF TREATING SYSTEMIC LUPUS ERYTHEMATOSUS

(71) Applicants: ZymoGenetics, Inc., Seattle, WA (US); University of Washington, Seattle, WA (US)

(72) Inventors: Stacey R. Dillon, Seattle, WA (US); Jane A. Gross, Seattle, WA (US); Keith B. Elkon, Seattle, WA (US)

(73) Assignees: ZYMOGENETICS, INC., Seattle, WA (US); UNIVERSITY OF WASHINTON, Seattle, WA (US)

( * ) Notice: Subject to any disclaimer, the term of this patent is extended or adjusted under 35 U.S.C. 154(b) by 0 days.

(21) Appl. No.: 14/192,911

(22) Filed: Feb. 28, 2014

(65) Prior Publication Data
US 2014/0220014 A1    Aug. 7, 2014

Related U.S. Application Data

(62) Division of application No. 12/429,502, filed on Apr. 24, 2009, now abandoned.

(60) Provisional application No. 61/047,869, filed on Apr. 25, 2008.

(51) Int. Cl.
*A61K 38/00* (2006.01)
*C07K 16/24* (2006.01)
*G01N 33/50* (2006.01)
*C07K 14/705* (2006.01)
*G01N 33/564* (2006.01)

(52) U.S. Cl.
CPC ........ *C07K 16/24* (2013.01); *C07K 14/70578* (2013.01); *G01N 33/5091* (2013.01); *G01N 33/564* (2013.01); *G01N 2333/70575* (2013.01); *G01N 2800/042* (2013.01); *G01N 2800/065* (2013.01); *G01N 2800/101* (2013.01); *G01N 2800/102* (2013.01); *G01N 2800/104* (2013.01); *G01N 2800/24* (2013.01); *G01N 2800/285* (2013.01); *G01N 2800/347* (2013.01)

(58) Field of Classification Search
None
See application file for complete search history.

(56) References Cited

U.S. PATENT DOCUMENTS

| 6,774,106 B2 | 8/2004 | Theill et al. |
| 7,371,388 B1 | 5/2008 | Ruben et al. |
| 7,501,497 B2 * | 3/2009 | Rixon et al. ............... 530/387.3 |
| 7,772,365 B2 | 8/2010 | Gross et al. |
| 2006/0034852 A1 | 2/2006 | Rixon et al. |

FOREIGN PATENT DOCUMENTS

| AU | 2006 201 471 A1 | 5/2006 |
| WO | WO 02/02641 A1 | 1/2002 |
| WO | WO 02/16312 A2 | 2/2002 |
| WO | WO 03/035846 A2 | 5/2003 |
| WO | WO 2005/000351 A2 | 1/2005 |
| WO | WO 2005/108986 A | 11/2005 |
| WO | WO 2006/068867 A | 6/2006 |

OTHER PUBLICATIONS

Dall'Era et al. Trial of Atacicept in Patients with Systemic Lupus Erythematosus (SLE). American College of Rheumatology, 2006 Annual Scientific Meeting, Abstract L19.*
Baker, Kevin P., et al., "Generation and Characterization of LymphoStat-B, a Human Monoclonal Antibody that Antagonizes the Bioactivities of B Lymphocyte Stimulator," *Arthritis & Rheumatism*, vol. 48, No. 11, (Nov. 2003), pp. 3253-3265.
Dillon, Stacey R., et al., "An APRIL to Remember: Novel TNF Ligands as Therapeutic Targets," *Nature Reviews*, vol. 5, (Mar. 2006), pp. 235-246.
Claudio, E., et al., "BAFF-Induced NEMO-Independent Processing of NF-κB2 in Maturing C Cells," *Nature Immunology*, (Oct. 2002), vol. 3, No. 10, pp. 958-965.
Cosman, D., "A Family of Ligands for the TNF Receptor Superfamily," *Stem Cells*, (1994), No. 12, pp. 440-455.
Gras, M-P., et al., "BCMAp: An Integral Membrane Protein in the Golgi Apparatus of Human Mature B Lymphocytes," *International Immunology*, (1995), vol. 7, No. 7, pp. 1093-1106.
Hatzoglou, A., et al., "TNF Receptor Family Member BCMA (B Cell Maturation) Associates with TNF Receptor-Associated Factor (TRAF) 1, TRAF2, and TRAF3 and Activates NF-κB, Elk-1, c-Jun N-Terminal Kinase, and p38 Mitogen-Activated Protein Kinase," *The Journal of Immunology*, (2000), vol. 165, pp. 1322-1330.
Kayagaki, N., et al., "BAFF/BLyS Receptor 3 Binds the B Cell Survival Factor BAFF Ligand through a Discrete Surface Loop and Promotes Processing of NF-kB2," *Immunity*, (Oct. 2002), vol. 10, pp. 515-524.
Ryan, M.C., et al., "Antibody Targeting of B-cell Maturation Antigen on Malignant Plasma Cells," *Mol. Cancer Ther.*, (2007), vol. 6, No. 11, pp. 3009-3018.
Smith, C.A., et al., "The TNF Receptor Superfamily of Cellular and Viral Proteins: Activation, Costimulation, and Death," *Cell*, (Mar. 1994), vol. 76, pp. 959-962.

(Continued)

*Primary Examiner* — Dong Jiang
(74) *Attorney, Agent, or Firm* — Womble Carlyle Sandridge & Rice LLP

(57) ABSTRACT

The present invention provides a method of measuring the levels of BCMA in a biological sample, specifically upon the B cell surface. The diagnostic assays are useful in predicting an individual's likelihood of developing or currently suffering from an autoimmune disease, such as SLE, and for methods for treating an individual clinically diagnosed with an autoimmune disease. This diagnostic test serves to predict a patient's likelihood to respond to a specific drug treatment, in particular treatment with BLyS antagonists, either singly or in combination with other immune suppressive drugs.

4 Claims, 20 Drawing Sheets

(56) References Cited

OTHER PUBLICATIONS

Carter, R.H., et al., "Expression and Occupancy Systemic lupus of BAFF-R on B Cells in Erythamatosus," *Arthritis & Rheumatism*, vol. 52, No. 12, Dec. 2005, pp. 3943-3954.

Thangarajh, M., et al., "The Expression of BAFF-Binding Receptors is not Altered in Multiple Sclerosis or Myasthenia Gravis," *Scandinavian Journal of Immunology*, vol. 65, No. 5, May 2007, pp. 461-466.

Zhang, D., et al., "Detection of the Expression Levels of B Cell Activating Factor and its Receptors in Patients with Systemic Lupus Erythematosus by Real-Time Fluorescence Quantitative Method," *Annual Meeting of the American Association for Clinical Chemistry*, Orlando, FL, Jul. 24-28, 2005.

Carter, R.H., et al., "Expression and Occupancy of BAFF-R on B Cells in Systemic Lupus Erythematosus," *Arthristis & Rhematism*, Dec. 2005, 52(12):3943-3954.

Yang, M., et al., "B Cell Maturation Antigen, the Receptor for a Proliferation-Inducing Ligand and B Cell-Activating Factor of the TNF Family, Induces Antigen Presentation in B Cells," *The Journal of Immunology*, 2005, 175: 2814-2824.

Darce, J., et al., "Regulated Expression of BAFF-Binding Receptors during Human B Cell Differentiation," *The Journal of Immunology*, 2004, vol. 103(2), pp. 689-694.

Novak, A., et al., "Expression of BCMA, TACI, BAFF-R in multiple myeloma: a mechanism for growth and survival," *BLOOD*, 2004, vol. 103(2), pp. 680-694.

\* cited by examiner

SEQUENCE LISTING

```
<160> NUMBER OF SEQ ID NOS: 26

<210> SEQ ID NO 1
<211> LENGTH: 1377
<212> TYPE: DNA
<213> ORGANISM: homo sapiens
<220> FEATURE:
<221> NAME/KEY: CDS
<222> LOCATION: (14)...(892)

<400> SEQUENCE: 1
agcatcctga gta atg agt ggc ctg ggc cgg agc agg cga ggt ggc cgg        49
            Met Ser Gly Leu Gly Arg Ser Arg Arg Gly Gly Arg
              1               5                   10 agc cgt gtg gac cag gag gag cgc ttt cca cag ggc ctg tgg acg ggg        97
Ser Arg Val Asp Gln Glu Glu Arg Phe Pro Gln Gly Leu Trp Thr Gly
         15                  20                  25 gtg gct atg aga tcc tgc ccc gaa gag cag tac tgg gat cct ctg ctg       145
Val Ala Met Arg Ser Cys Pro Glu Glu Gln Tyr Trp Asp Pro Leu Leu
     30                  35                  40 ggt acc tgc atg tcc tgc aaa acc att tgc aac cat cag agc cag cgc       193
Gly Thr Cys Met Ser Cys Lys Thr Ile Cys Asn His Gln Ser Gln Arg
 45                  50                  55                  60 acc tgt gca gcc ttc tgc agg tca ctc agc tgc cgc aag gag caa ggc       241
Thr Cys Ala Ala Phe Cys Arg Ser Leu Ser Cys Arg Lys Glu Gln Gly
                 65                  70                  75 aag ttc tat gac cat ctc ctg agg gac tgc atc agc tgt gcc tcc atc       289
Lys Phe Tyr Asp His Leu Leu Arg Asp Cys Ile Ser Cys Ala Ser Ile
             80                  85                  90
```

| | | |
|---|---|---|
| tgt gga cag cac cct aag caa tgt gca tac ttc tgt gag aac aag ctc | | 337 |
| Cys Gly Gln His Pro Lys Gln Cys Ala Tyr Phe Cys Glu Asn Lys Leu | | |
| 95 100 105 | | |
| agg agc cca gtg aac ctt cca cca gag ctc agg aga cag cgg agt gga | | 385 |
| Arg Ser Pro Val Asn Leu Pro Pro Glu Leu Arg Arg Gln Arg Ser Gly | | |
| 110 115 120 | | |
| gaa gtt gaa aac aat tca gac aac tcg gga agg tac caa gga ttg gag | | 433 |
| Glu Val Glu Asn Asn Ser Asp Asn Ser Gly Arg Tyr Gln Gly Leu Glu | | |
| 125 130 135 140 | | |
| cac aga ggc tca gaa gca agt cca gct ctc ccg ggg ctg aag ctg agt | | 481 |
| His Arg Gly Ser Glu Ala Ser Pro Ala Leu Pro Gly Leu Lys Leu Ser | | |
| 145 150 155 | | |
| gca gat cag gtg gcc ctg gtc tac agc acg ctg ggg ctc tgc ctg tgt | | 529 |
| Ala Asp Gln Val Ala Leu Val Tyr Ser Thr Leu Gly Leu Cys Leu Cys | | |
| 160 165 170 | | |
| gcc gtc ctc tgc tgc ttc ctg gtg gcg gtg gcc tgc ttc ctc aag aag | | 577 |
| Ala Val Leu Cys Cys Phe Leu Val Ala Val Ala Cys Phe Leu Lys Lys | | |
| 175 180 185 | | |
| agg ggg gat ccc tgc tcc tgc cag ccc cgc tca agg ccc cgt caa agt | | 625 |
| Arg Gly Asp Pro Cys Ser Cys Gln Pro Arg Ser Arg Pro Arg Gln Ser | | |
| 190 195 200 | | |
| ccg gcc aag tct tcc cag gat cac gcg atg gaa gcc ggc agc cct gtg | | 673 |
| Pro Ala Lys Ser Ser Gln Asp His Ala Met Glu Ala Gly Ser Pro Val | | |
| 205 210 215 220 | | |
| agc aca tcc ccc gag cca gtg gag acc tgc agc ttc tgc ttc cct gag | | 721 |
| Ser Thr Ser Pro Glu Pro Val Glu Thr Cys Ser Phe Cys Phe Pro Glu | | |
| 225 230 235 | | |
| tgc agg gcg ccc acg cag gag agc gca gtc acg cct ggg acc ccc gac | | 769 |
| Cys Arg Ala Pro Thr Gln Glu Ser Ala Val Thr Pro Gly Thr Pro Asp | | |
| 240 245 250 | | |
| ccc act tgt gct gga agg tgg ggg tgc cac acc agg acc aca gtc ctg | | 817 |
| Pro Thr Cys Ala Gly Arg Trp Gly Cys His Thr Arg Thr Thr Val Leu | | |
| 255 260 265 | | |
| cag cct tgc cca cac atc cca gac agt ggc ctt ggc att gtg tgt gtg | | 865 |
| Gln Pro Cys Pro His Ile Pro Asp Ser Gly Leu Gly Ile Val Cys Val | | |
| 270 275 280 | | |
| cct gcc cag gag ggg ggc cca ggt gca taaatggggg tcagggaggg | | 912 |
| Pro Ala Gln Glu Gly Gly Pro Gly Ala | | |
| 285 290 | | |
| aaaggaggag ggagagagat ggagaggagg ggagagagaa agagaggtgg ggagagggga | | 972 |
| gagagatatg aggagagaga gacagaggag gcagaaaggg agagaaacag aggagacaga | | 1032 |
| gagggagaga gagacagagg gagagagaga cagaggggga gagaggcaga gagggaaaga | | 1092 |
| ggcagagaag gaaagagaca ggcagagaag gagagaggca gagagggaga gaggcagaga | | 1152 |
| gggagagagg cagagagaca gagagggaga gagggacaga gagagataga gcaggaggtc | | 1212 |
| ggggcactct gagtcccagt tcccagtgca gctgtaggtc gtcatcacct aaccacacgt | | 1272 |
| gcaataaagt cctcgtgcct gctgctcaca gcccccgaga gcccctcctc ctggagaata | | 1332 |
| aaacctttgg cagctgccct tcctcaaaaa aaaaaaaaaa aaaaa | | 1377 |

<210> SEQ ID NO 2
<211> LENGTH: 293
<212> TYPE: PRT
<213> ORGANISM: homo sapiens

<400> SEQUENCE: 2

Met Ser Gly Leu Gly Arg Ser Arg Arg Gly Gly Arg Ser Arg Val Asp
1               5                   10                  15

```
Gln Glu Glu Arg Phe Pro Gln Gly Leu Trp Thr Gly Val Ala Met Arg
         20                  25                  30

Ser Cys Pro Glu Glu Gln Tyr Trp Asp Pro Leu Leu Gly Thr Cys Met
     35                  40                  45

Ser Cys Lys Thr Ile Cys Asn His Gln Ser Gln Arg Thr Cys Ala Ala
 50                  55                  60

Phe Cys Arg Ser Leu Ser Cys Arg Lys Glu Gln Gly Lys Phe Tyr Asp
 65                  70                  75                  80

His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 3
<211> LENGTH: 586
<212> TYPE: DNA
<213> ORGANISM: homo sapiens
<220> FEATURE:
<221> NAME/KEY: CDS
<222> LOCATION: (27)...(578)

<400> SEQUENCE: 3
gcagcttgtg cggcggcgtc ggcacc atg agg cga ggg ccc cgg agc ctg cgg      53
                              Met Arg Arg Gly Pro Arg Ser Leu Arg
                                1               5 ggc agg gac gcg cca gcc ccc acg ccc tgc gtc ccg gcc gag tgc ttc      101
Gly Arg Asp Ala Pro Ala Pro Thr Pro Cys Val Pro Ala Glu Cys Phe
 10                  15                  20                  25 gac ctg ctg gtc cgc cac tgc gtg gcc tgc ggg ctc ctg cgc acg ccg      149
Asp Leu Leu Val Arg His Cys Val Ala Cys Gly Leu Leu Arg Thr Pro
                 30                  35                  40 cgg ccg aaa ccg gcc ggg gcc agc agc cct gcg ccc agg acg gcg ctg      197
```

```
cag ccg cag gag tcg gtg ggc gcg ggg gcc ggc gag gcg gcg ctg ccc     245
Gln Pro Gln Glu Ser Val Gly Ala Gly Ala Gly Glu Ala Ala Leu Pro
        60                  65                  70 ctg ccc ggg ctg ctc ttt ggc gcc ccc gcg ctg ctg ggc ctg gca ctg     293
Leu Pro Gly Leu Leu Phe Gly Ala Pro Ala Leu Leu Gly Leu Ala Leu
    75                  80                  85 gtc ctg gcg ctg gtc ctg gtg ggt ctg gtg agc tgg agg cgg cga cag     341
Val Leu Ala Leu Val Leu Val Gly Leu Val Ser Trp Arg Arg Arg Gln
90                  95                 100                 105 cgg cgg ctt cgc ggc gcg tcc tcc gca gag gcc ccc gac gga gac aag     389
Arg Arg Leu Arg Gly Ala Ser Ser Ala Glu Ala Pro Asp Gly Asp Lys
            110                 115                 120 gac gcc cca gag ccc ctg gac aag gtc atc att ctg tct ccg gga atc     437
Asp Ala Pro Glu Pro Leu Asp Lys Val Ile Ile Leu Ser Pro Gly Ile
        125                 130                 135 tct gat gcc aca gct cct gcc tgg cct cct cct ggg gaa gac cca gga     485
Ser Asp Ala Thr Ala Pro Ala Trp Pro Pro Pro Gly Glu Asp Pro Gly
    140                 145                 150 acc acc cca cct ggc cac agt gtc cct gtg cca gcc aca gag ctg ggc     533
Thr Thr Pro Pro Gly His Ser Val Pro Val Pro Ala Thr Glu Leu Gly
155                 160                 165 tcc act gaa ctg gtg acc acc aag acg gcc ggc cct gag caa caa         578
Ser Thr Glu Leu Val Thr Thr Lys Thr Ala Gly Pro Glu Gln Gln
170                 175                 180 tagcaggg                                                            586
```

<210> SEQ ID NO 4
<211> LENGTH: 184
<212> TYPE: PRT
<213> ORGANISM: homo sapiens

<400> SEQUENCE: 4

```
Met Arg Arg Gly Pro Arg Ser Leu Arg Gly Arg Asp Ala Pro Ala Pro
 1               5                  10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180
```

<210> SEQ ID NO 5
<211> LENGTH: 995
<212> TYPE: DNA
<213> ORGANISM: homo sapiens
<220> FEATURE:
<221> NAME/KEY: CDS
<222> LOCATION: (219)...(770)

<400> SEQUENCE: 5

```
aagactcaaa cttagaaact tgaattagat gtggtattca aatccttacg tgccgcgaag      60
acacagacag cccccgtaag aacccacgaa gcaggcgaag ttcattgttc tcaacattct     120
agctgctctt gctgcatttg ctctggaatt cttgtagaga tattacttgt ccttccaggc     180
tgttctttct gtagctccct gtttctctt tgtgatc atg ttg cag atg gct ggg       236
                                         Met Leu Gln Met Ala Gly
                                           1               5 cag tgc tcc caa aat gaa tat ttt gac agt ttg ttg cat gct tgc ata       284
Gln Cys Ser Gln Asn Glu Tyr Phe Asp Ser Leu Leu His Ala Cys Ile
         10                  15                  20 cct tgt caa ctt cga tgt tct tct aat act cct cct cta aca tgt cag       332
Pro Cys Gln Leu Arg Cys Ser Ser Asn Thr Pro Pro Leu Thr Cys Gln
     25                  30                  35 cgt tat tgt aat gca agt gtg acc aat tca gtg aaa gga acg aat gcg       380
Arg Tyr Cys Asn Ala Ser Val Thr Asn Ser Val Lys Gly Thr Asn Ala
 40                  45                  50 att ctc tgg acc tgt ttg gga ctg agc tta ata att tct ttg gca gtt       428
Ile Leu Trp Thr Cys Leu Gly Leu Ser Leu Ile Ile Ser Leu Ala Val
 55                  60                  65                  70 ttc gtg cta atg ttt ttg cta agg aag ata agc tct gaa cca tta aag       476
Phe Val Leu Met Phe Leu Leu Arg Lys Ile Ser Ser Glu Pro Leu Lys
                 75                  80                  85 gac gag ttt aaa aac aca gga tca ggt ctc ctg ggc atg gct aac att       524
Asp Glu Phe Lys Asn Thr Gly Ser Gly Leu Leu Gly Met Ala Asn Ile
             90                  95                 100 gac ctg gaa aag agc agg act ggt gat gaa att att ctt ccg aga ggc       572
Asp Leu Glu Lys Ser Arg Thr Gly Asp Glu Ile Ile Leu Pro Arg Gly
        105                 110                 115 ctc gag tac acg gtg gaa gaa tgc acc tgt gaa gac tgc atc aag agc       620
Leu Glu Tyr Thr Val Glu Glu Cys Thr Cys Glu Asp Cys Ile Lys Ser
    120                 125                 130 aaa ccg aag gtc gac tct gac cat tgc ttt cca ctc cca gct atg gag       668
Lys Pro Lys Val Asp Ser Asp His Cys Phe Pro Leu Pro Ala Met Glu
135                 140                 145                 150 gaa ggc gca acc att ctt gtc acc acg aaa acg aat gac tat tgc aag       716
Glu Gly Ala Thr Ile Leu Val Thr Thr Lys Thr Asn Asp Tyr Cys Lys
                155                 160                 165 agc ctg cca gct gct ttg agt gct acg gag ata gag aaa tca att tct       764
Ser Leu Pro Ala Ala Leu Ser Ala Thr Glu Ile Glu Lys Ser Ile Ser
            170                 175                 180 gct agg taattaacca tttcgactcg agcagtgcca ctttaaaaat cttttgtcag        820
Ala Arg aatagatgat gtgtcagatc tctttaggat gactgtattt tcagttgcc gatacagctt      880 tttgtcctct aactgtggaa actctttatg ttagatatat ttctctaggt tactgttggg     940
agcttaatgg tagaaacttc cttggtttca tgattaaagt cttttttttt cctga          995
```

<210> SEQ ID NO 6
<211> LENGTH: 184

```
<212> TYPE: PRT
<213> ORGANISM: homo sapiens

<400> SEQUENCE: 6

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 7
<211> LENGTH: 1149
<212> TYPE: DNA
<213> ORGANISM: homo sapiens
<220> FEATURE:
<221> NAME/KEY: CDS
<222> LOCATION: (173)...(1023)

<400> SEQUENCE: 7
gaattcggca cgaggcagaa aggagaaaat tcaggataac tctcctgagg ggtgagccaa      60
gccctgccat gtagtgcacg caggacatca acaaacacag ataacaggaa atgatccatt     120
ccctgtggtc acttattcta aaggcccaa ccttcaaagt tcaagtagtg at atg gat      178
                                                       Met Asp
                                                         1 gac tcc aca gaa agg gag cag tca cgc ctt act tct tgc ctt aag aaa      226
Asp Ser Thr Glu Arg Glu Gln Ser Arg Leu Thr Ser Cys Leu Lys Lys
        5                   10                  15 aga gaa gaa atg aaa ctg aag gag tgt gtt tcc atc ctc cca cgg aag      274
Arg Glu Glu Met Lys Leu Lys Glu Cys Val Ser Ile Leu Pro Arg Lys
    20                  25                  30 gaa agc ccc tct gtc cga tcc tcc aaa gac gga aag ctg ctg gct gca      322
Glu Ser Pro Ser Val Arg Ser Ser Lys Asp Gly Lys Leu Leu Ala Ala
35                  40                  45                  50 acc ttg ctg ctg gca ctg ctg tct tgc tgc ctc acg gtg gtg tct ttc      370
Thr Leu Leu Leu Ala Leu Leu Ser Cys Cys Leu Thr Val Val Ser Phe
                55                  60                  65 tac cag gtg gcc gcc ctg caa ggg gac ctg gcc agc ctc cgg gca gag      418
Tyr Gln Val Ala Ala Leu Gln Gly Asp Leu Ala Ser Leu Arg Ala Glu
            70                  75                  80
```

```
ctg cag ggc cac cac gcg gag aag ctg cca gca gga gca gga gcc ccc      466
Leu Gln Gly His His Ala Glu Lys Leu Pro Ala Gly Ala Gly Ala Pro
            85                  90                  95 aag gcc ggc ctg gag gaa gct cca gct gtc acc gcg gga ctg aaa atc      514
Lys Ala Gly Leu Glu Glu Ala Pro Ala Val Thr Ala Gly Leu Lys Ile
100                 105                 110 ttt gaa cca cca gct cca gga gaa ggc aac tcc agt cag aac agc aga      562
Phe Glu Pro Pro Ala Pro Gly Glu Gly Asn Ser Ser Gln Asn Ser Arg
115                 120                 125                 130 aat aag cgt gcc gtt cag ggt cca gaa gaa aca gtc act caa gac tgc      610
Asn Lys Arg Ala Val Gln Gly Pro Glu Glu Thr Val Thr Gln Asp Cys
                135                 140                 145 ttg caa ctg att gca gac agt gaa aca cca act ata caa aaa gga tct      658
Leu Gln Leu Ile Ala Asp Ser Glu Thr Pro Thr Ile Gln Lys Gly Ser
        150                 155                 160 tac aca ttt gtt cca tgg ctt ctc agc ttt aaa agg gga agt gcc cta      706
Tyr Thr Phe Val Pro Trp Leu Leu Ser Phe Lys Arg Gly Ser Ala Leu
    165                 170                 175 gaa gaa aaa gag aat aaa ata ttg gtc aaa gaa act ggt tac ttt ttt      754
Glu Glu Lys Glu Asn Lys Ile Leu Val Lys Glu Thr Gly Tyr Phe Phe
180                 185                 190 ata tat ggt cag gtt tta tat act gat aag acc tac gcc atg gga cat      802
Ile Tyr Gly Gln Val Leu Tyr Thr Asp Lys Thr Tyr Ala Met Gly His
195                 200                 205                 210 cta att cag agg aag aag gtc cat gtc ttt ggg gat gaa ttg agt ctg      850
Leu Ile Gln Arg Lys Lys Val His Val Phe Gly Asp Glu Leu Ser Leu
        215                 220                 225 gtg act ttg ttt cga tgt att caa aat atg cct gaa aca cta ccc aat      898
Val Thr Leu Phe Arg Cys Ile Gln Asn Met Pro Glu Thr Leu Pro Asn
    230                 235                 240 aat tcc tgc tat tca gct ggc att gca aaa ctg gaa gaa gga gat gaa      946
Asn Ser Cys Tyr Ser Ala Gly Ile Ala Lys Leu Glu Glu Gly Asp Glu
                245                 250                 255 ctc caa ctt gca ata cca aga gaa aat gca caa ata tca ctg gat gga      994
Leu Gln Leu Ala Ile Pro Arg Glu Asn Ala Gln Ile Ser Leu Asp Gly
            260                 265                 270 gat gtc aca ttt ttt ggt gca ttg aaa ct gctgtgacct acttacacca        1043
Asp Val Thr Phe Phe Gly Ala Leu Lys
275                 280 tgtctgtagc tattttcctc cctttctctg tacctctaag aagaaagaat ctaactgaaa   1103
ataccaaaaa aaaaaaaaaa aaaaaaaaaa ccctcgagcg gccgcc                  1149

<210> SEQ ID NO 8
<211> LENGTH: 283
<212> TYPE: PRT
<213> ORGANISM: homo sapiens

<400> SEQUENCE: 8

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80
```

```
Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys
        275                 280
```

<210> SEQ ID NO 9
<211> LENGTH: 1680
<212> TYPE: DNA
<213> ORGANISM: mus musculus
<220> FEATURE:
<221> NAME/KEY: CDS
<222> LOCATION: (164)...(1093)

<400> SEQUENCE: 9

```
tactcactat agggctcgag cggccgcccg ggcaggtgct cctgggggaa cccagccctg      60
ccatgctctg agggcagtct cccaggacac agatgacagg aaatgaccca cccctgtggt     120
cacttactcc aaaggcctag accttcaaag tgctcctcgt gga atg gat gag tct      175
                                              Met Asp Glu Ser
                                                1 gca aag acc ctg cca cca ccg tgc ctc tgt ttt tgc tcc gag aaa gga      223
Ala Lys Thr Leu Pro Pro Pro Cys Leu Cys Phe Cys Ser Glu Lys Gly
 5                  10                  15                  20 gaa gat atg aaa gtg gga tat gat ccc atc act ccg cag aag gag gag      271
Glu Asp Met Lys Val Gly Tyr Asp Pro Ile Thr Pro Gln Lys Glu Glu
             25                  30                  35 ggt gcc tgg ttt ggg atc tgc agg gat gga agg ctg ctg gct gct acc      319
Gly Ala Trp Phe Gly Ile Cys Arg Asp Gly Arg Leu Leu Ala Ala Thr
         40                  45                  50 ctc ctg ctg gcc ctg ttg tcc agc agt ttc aca gcg atg tcc ttg tac      367
Leu Leu Leu Ala Leu Leu Ser Ser Ser Phe Thr Ala Met Ser Leu Tyr
     55                  60                  65 cag ttg gct gcc ttg caa gca gac ctg atg aac ctg cgc atg gag ctg      415
Gln Leu Ala Ala Leu Gln Ala Asp Leu Met Asn Leu Arg Met Glu Leu
 70                  75                  80
```

```
cag agc tac cga ggt tca gca aca cca gcc gcc gcg ggt gct cca gag    463
Gln Ser Tyr Arg Gly Ser Ala Thr Pro Ala Ala Ala Gly Ala Pro Glu
 85                  90                  95                 100 ttg acc gct gga gtc aaa ctc ctg aca ccg gca gct cct cga ccc cac    511
Leu Thr Ala Gly Val Lys Leu Leu Thr Pro Ala Ala Pro Arg Pro His
                105                 110                 115 aac tcc agc cgc ggc cac agg aac aga cgc gct ttc cag gga cca gag    559
Asn Ser Ser Arg Gly His Arg Asn Arg Arg Ala Phe Gln Gly Pro Glu
            120                 125                 130 gaa aca gaa caa gat gta gac ctc tca gct cct cct gca cca tgc ctg    607
Glu Thr Glu Gln Asp Val Asp Leu Ser Ala Pro Pro Ala Pro Cys Leu
        135                 140                 145 cct gga tgc cgc cat tct caa cat gat gat aat gga atg aac ctc aga    655
Pro Gly Cys Arg His Ser Gln His Asp Asp Asn Gly Met Asn Leu Arg
    150                 155                 160 aac atc att caa gac tgt ctg cag ctg att gca gac agc gac acg ccg    703
Asn Ile Ile Gln Asp Cys Leu Gln Leu Ile Ala Asp Ser Asp Thr Pro
165                 170                 175                 180 act ata cga aaa gga act tac aca ttt gtt cca tgg ctt ctc agc ttt    751
Thr Ile Arg Lys Gly Thr Tyr Thr Phe Val Pro Trp Leu Leu Ser Phe
                185                 190                 195 aaa aga gga aat gcc ttg gag gag aaa gag aac aaa ata gtg gtg agg    799
Lys Arg Gly Asn Ala Leu Glu Glu Lys Glu Asn Lys Ile Val Val Arg
            200                 205                 210 caa aca ggc tat ttc ttc atc tac agc cag gtt cta tac acg gac ccc    847
Gln Thr Gly Tyr Phe Phe Ile Tyr Ser Gln Val Leu Tyr Thr Asp Pro
        215                 220                 225 atc ttt gct atg ggt cat gtc atc cag agg aag aaa gta cac gtc ttt    895
Ile Phe Ala Met Gly His Val Ile Gln Arg Lys Lys Val His Val Phe
    230                 235                 240 ggg gac gag ctg agc ctg gtg acc ctg ttc cga tgt att cag aat atg    943
Gly Asp Glu Leu Ser Leu Val Thr Leu Phe Arg Cys Ile Gln Asn Met
245                 250                 255                 260 ccc aaa aca ctg ccc aac aat tcc tgc tac tcg gct ggc atc gcg agg    991
Pro Lys Thr Leu Pro Asn Asn Ser Cys Tyr Ser Ala Gly Ile Ala Arg
                265                 270                 275 ctg gaa gaa gga gat gag att cag ctt gca att cct cgg gag aat gca   1039
Leu Glu Glu Gly Asp Glu Ile Gln Leu Ala Ile Pro Arg Glu Asn Ala
            280                 285                 290 cag att tca cgc aac gga gac gac acc ttc ttt ggt gcc cta aaa ctg   1087
Gln Ile Ser Arg Asn Gly Asp Asp Thr Phe Phe Gly Ala Leu Lys Leu
        295                 300                 305 ctg taa ctcacttgct ggagtgcgtg atcccttcc ctcgtcttct ctgtacctcc     1143
Leu  * gagggagaaa cagacgactg gaaaaactaa agatgggga aagccgtcag cgaaagtttt   1203
ctcgtgaccc gttgaatctg atccaaacca ggaaatataa cagacagcca caaccgaagt   1263
gtgccatgtg agttatgaga acggagccc gcgctcagaa agaccggatg aggaagaccg    1323 tttctccag tcctttgcca acacgcaccg caacctttgct ttttgccttg ggtgacacat   1383
gttcagaatg cagggagatt tccttgtttt gcgatttgcc atgagaagag ggcccacaac   1443
tgcaggtcac tgaagcattc acgctaagtc tcaggattta ctctcccttc tcatgctaag   1503
tacacacacg ctcttttcca ggtaatacta tgggatacta tggaaggtt gtttgttttt   1563 aaatctagaa gtcttgaact ggcaatagac aaaaatcctt ataaattcaa gtgtaaaata   1623
aacttaatta aaaaggtaaa aaaaaaaaaa aaaaaaaaaa aaaaaaaaaa aaaaaaa     1680

<210> SEQ ID NO 10
```

```
<211> LENGTH: 309
<212> TYPE: PRT
<213> ORGANISM: mus musculus

<400> SEQUENCE: 10

Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Leu Ala Leu Leu Ser Ser Ser Phe Thr Ala
    50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305

<210> SEQ ID NO 11
<211> LENGTH: 185
<212> TYPE: PRT
<213> ORGANISM: homo sapiens

<400> SEQUENCE: 11

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30
```

Val Ala Cys Gly Leu Leu Arg Thr Pro Arg Pro Lys Pro Ala Gly Ala
            35                  40                  45

Ala Ser Ser Pro Ala Pro Arg Thr Ala Leu Gln Pro Gln Glu Ser Val
    50                  55                  60

Gly Ala Gly Ala Gly Glu Ala Ala Leu Pro Leu Pro Gly Leu Leu Phe
65                  70                  75                  80

Gly Ala Pro Ala Leu Leu Gly Leu Ala Leu Val Leu Ala Leu Val Leu
                85                  90                  95

Val Gly Leu Val Ser Trp Arg Arg Gln Arg Arg Leu Arg Gly Ala
            100                 105                 110

Ser Ser Ala Glu Ala Pro Asp Gly Asp Lys Asp Ala Pro Glu Pro Leu
            115                 120                 125

Asp Lys Val Ile Ile Leu Ser Pro Gly Ile Ser Asp Ala Thr Ala Pro
130                 135                 140

Ala Trp Pro Pro Pro Gly Glu Asp Pro Gly Thr Thr Pro Pro Gly His
145                 150                 155                 160

Ser Val Pro Val Pro Ala Thr Glu Leu Gly Ser Thr Glu Leu Val Thr
                165                 170                 175

Thr Lys Thr Ala Gly Pro Glu Gln Gln
            180                 185

<210> SEQ ID NO 12
<211> LENGTH: 247
<212> TYPE: PRT
<213> ORGANISM: homo sapiens

<400> SEQUENCE: 12

Met Ser Gly Leu Gly Arg Ser Arg Arg Gly Gly Arg Ser Arg Val Asp
1               5                   10                  15

Gln Glu Glu Arg Trp Ser Leu Ser Cys Arg Lys Glu Gln Gly Lys Phe
            20                  25                  30

Tyr Asp His Leu Leu Arg Asp Cys Ile Ser Cys Ala Ser Ile Cys Gly
            35                  40                  45

Gln His Pro Lys Gln Cys Ala Tyr Phe Cys Glu Asn Lys Leu Arg Ser
    50                  55                  60

Pro Val Asn Leu Pro Pro Glu Leu Arg Arg Gln Arg Ser Gly Glu Val
65                  70                  75                  80

Glu Asn Asn Ser Asp Asn Ser Gly Arg Tyr Gln Gly Leu Glu His Arg
                85                  90                  95

Gly Ser Glu Ala Ser Pro Ala Leu Pro Gly Leu Lys Leu Ser Ala Asp
            100                 105                 110

Gln Val Ala Leu Val Tyr Ser Thr Leu Gly Leu Cys Leu Cys Ala Val
            115                 120                 125

Leu Cys Cys Phe Leu Val Ala Val Ala Cys Phe Leu Lys Lys Arg Gly
    130                 135                 140

Asp Pro Cys Ser Cys Gln Pro Arg Ser Arg Pro Arg Gln Ser Pro Ala
145                 150                 155                 160

Lys Ser Ser Gln Asp His Ala Met Glu Ala Gly Ser Pro Val Ser Thr
                165                 170                 175

Ser Pro Glu Pro Val Glu Thr Cys Ser Phe Cys Phe Pro Glu Cys Arg
            180                 185                 190

Ala Pro Thr Gln Glu Ser Ala Val Thr Pro Gly Thr Pro Asp Pro Thr
            195                 200                 205

Cys Ala Gly Arg Trp Gly Cys His Thr Arg Thr Thr Val Leu Gln Pro

```
                210                 215                 220
Cys Pro His Ile Pro Asp Ser Gly Leu Gly Ile Val Cys Val Pro Ala
225                 230                 235                 240

Gln Glu Gly Gly Pro Gly Ala
                245

<210> SEQ ID NO 13
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 13

Glu Cys Phe Asp Leu Leu Val Arg Ala Trp Val Pro Cys Ser Val Leu
1               5                   10                  15

Lys

<210> SEQ ID NO 14
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 14

Glu Cys Phe Asp Leu Leu Val Arg His Trp Val Pro Cys Gly Leu Leu
1               5                   10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 15

Glu Cys Phe Asp Leu Leu Val Arg Arg Trp Val Pro Cys Glu Met Leu
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 16

Glu Cys Phe Asp Leu Leu Val Arg Ser Trp Val Pro Cys His Met Leu
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 17

Glu Cys Phe Asp Leu Leu Val Arg His Trp Val Ala Cys Gly Leu Leu
```

Arg

```
<210> SEQ ID NO 18
<211> LENGTH: 1214
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1192)

<400> SEQUENCE: 18
```

| | | | | | | | | | | | | |
|---|---|---|---|---|---|---|---|---|---|---|---|---|
| tattaggccg gccacc | atg | gat | gca | atg | aag | aga | ggg | ctc | tgc | tgt | gtg ctg | 52 |
| | Met | Asp | Ala | Met | Lys | Arg | Gly | Leu | Cys | Cys | Val Leu | |
| | 1 | | | 5 | | | | | 10 | | | |

| ctg | ctg | tgt | ggc | gcc | gtc | ttc | gtt | tcg | ctc | agc | cag | gaa | atc | cat | gcc | 100 |
|---|---|---|---|---|---|---|---|---|---|---|---|---|---|---|---|---|
| Leu | Leu | Cys | Gly | Ala | Val | Phe | Val | Ser | Leu | Ser | Gln | Glu | Ile | His | Ala | |
| | 15 | | | | 20 | | | | | 25 | | | | | | |

| gag | ttg | aga | cgc | ttc | cgt | aga | gct | atg | aga | tcc | tgc | ccc | gaa | gag | cag | 148 |
|---|---|---|---|---|---|---|---|---|---|---|---|---|---|---|---|---|
| Glu | Leu | Arg | Arg | Phe | Arg | Arg | Ala | Met | Arg | Ser | Cys | Pro | Glu | Glu | Gln | |
| 30 | | | | | 35 | | | | | 40 | | | | | | |

| tac | tgg | gat | cct | ctg | ctg | ggt | acc | tgc | atg | tcc | tgc | aaa | acc | att | tgc | 196 |
|---|---|---|---|---|---|---|---|---|---|---|---|---|---|---|---|---|
| Tyr | Trp | Asp | Pro | Leu | Leu | Gly | Thr | Cys | Met | Ser | Cys | Lys | Thr | Ile | Cys | |
| 45 | | | | | 50 | | | | | 55 | | | | | 60 | |

| aac | cat | cag | agc | cag | cgc | acc | tgt | gca | gcc | ttc | tgc | agg | tca | ctc | agc | 244 |
|---|---|---|---|---|---|---|---|---|---|---|---|---|---|---|---|---|
| Asn | His | Gln | Ser | Gln | Arg | Thr | Cys | Ala | Ala | Phe | Cys | Arg | Ser | Leu | Ser | |
| | | | | 65 | | | | | 70 | | | | | 75 | | |

| tgc | cgc | aag | gag | caa | ggc | aag | ttc | tat | gac | cat | ctc | ctg | agg | gac | tgc | 292 |
|---|---|---|---|---|---|---|---|---|---|---|---|---|---|---|---|---|
| Cys | Arg | Lys | Glu | Gln | Gly | Lys | Phe | Tyr | Asp | His | Leu | Leu | Arg | Asp | Cys | |
| | | | 80 | | | | | 85 | | | | | 90 | | | |

| atc | agc | tgt | gcc | tcc | atc | tgt | gga | cag | cac | cct | aag | caa | tgt | gca | tac | 340 |
|---|---|---|---|---|---|---|---|---|---|---|---|---|---|---|---|---|
| Ile | Ser | Cys | Ala | Ser | Ile | Cys | Gly | Gln | His | Pro | Lys | Gln | Cys | Ala | Tyr | |
| | | 95 | | | | | 100 | | | | | 105 | | | | |

| ttc | tgt | gag | aac | aag | ctc | agg | agc | cca | gtg | aac | ctt | cca | cca | gag | ctc | 388 |
|---|---|---|---|---|---|---|---|---|---|---|---|---|---|---|---|---|
| Phe | Cys | Glu | Asn | Lys | Leu | Arg | Ser | Pro | Val | Asn | Leu | Pro | Pro | Glu | Leu | |
| 110 | | | | | 115 | | | | | 120 | | | | | | |

| agg | aga | cag | cgg | agt | gga | gaa | gtt | gaa | aac | aat | tca | gac | aac | tcg | gga | 436 |
|---|---|---|---|---|---|---|---|---|---|---|---|---|---|---|---|---|
| Arg | Arg | Gln | Arg | Ser | Gly | Glu | Val | Glu | Asn | Asn | Ser | Asp | Asn | Ser | Gly | |
| 125 | | | | | 130 | | | | | 135 | | | | | 140 | |

| agg | tac | caa | gga | ttg | gag | cac | aga | ggc | tca | gaa | gca | agt | cca | gct | ctc | 484 |
|---|---|---|---|---|---|---|---|---|---|---|---|---|---|---|---|---|
| Arg | Tyr | Gln | Gly | Leu | Glu | His | Arg | Gly | Ser | Glu | Ala | Ser | Pro | Ala | Leu | |
| | | | | 145 | | | | | 150 | | | | | 155 | | |

| cca | ggt | ctc | aag | gag | ccc | aaa | tct | tca | gac | aaa | act | cac | aca | tgc | cca | 532 |
|---|---|---|---|---|---|---|---|---|---|---|---|---|---|---|---|---|
| Pro | Gly | Leu | Lys | Glu | Pro | Lys | Ser | Ser | Asp | Lys | Thr | His | Thr | Cys | Pro | |
| | | | 160 | | | | | 165 | | | | | 170 | | | |

| ccg | tgc | cca | gca | cct | gaa | gcc | gag | ggg | gca | ccg | tca | gtc | ttc | ctc | ttc | 580 |
|---|---|---|---|---|---|---|---|---|---|---|---|---|---|---|---|---|
| Pro | Cys | Pro | Ala | Pro | Glu | Ala | Glu | Gly | Ala | Pro | Ser | Val | Phe | Leu | Phe | |
| | | 175 | | | | | 180 | | | | | 185 | | | | |

| ccc | cca | aaa | ccc | aag | gac | acc | ctc | atg | atc | tcc | cgg | acc | cct | gag | gtc | 628 |
|---|---|---|---|---|---|---|---|---|---|---|---|---|---|---|---|---|
| Pro | Pro | Lys | Pro | Lys | Asp | Thr | Leu | Met | Ile | Ser | Arg | Thr | Pro | Glu | Val | |
| 190 | | | | | 195 | | | | | 200 | | | | | | |

| aca | tgc | gtg | gtg | gtg | gac | gtg | agc | cac | gaa | gac | cct | gag | gtc | aag | ttc | 676 |
|---|---|---|---|---|---|---|---|---|---|---|---|---|---|---|---|---|
| Thr | Cys | Val | Val | Val | Asp | Val | Ser | His | Glu | Asp | Pro | Glu | Val | Lys | Phe | |
| 205 | | | | | 210 | | | | | 215 | | | | | 220 | |

| aac | tgg | tac | gtg | gac | ggc | gtg | gag | gtg | cat | aat | gcc | aag | aca | aag | ccg | 724 |
|---|---|---|---|---|---|---|---|---|---|---|---|---|---|---|---|---|
| Asn | Trp | Tyr | Val | Asp | Gly | Val | Glu | Val | His | Asn | Ala | Lys | Thr | Lys | Pro | |
| | | | | 225 | | | | | 230 | | | | | 235 | | |

| cgg | gag | gag | cag | tac | aac | agc | acg | tac | cgt | gtg | gtc | agc | gtc | ctc | acc | 772 |
|---|---|---|---|---|---|---|---|---|---|---|---|---|---|---|---|---|
| Arg | Glu | Glu | Gln | Tyr | Asn | Ser | Thr | Tyr | Arg | Val | Val | Ser | Val | Leu | Thr | |

```
gtc ctg cac cag gac tgg ctg aat ggc aag gag tac aag tgc aag gtc      820
Val Leu His Gln Asp Trp Leu Asn Gly Lys Glu Tyr Lys Cys Lys Val
            255                 260                 265 tcc aac aaa gcc ctc cca tcc tcc atc gag aaa acc atc tcc aaa gcc      868
Ser Asn Lys Ala Leu Pro Ser Ser Ile Glu Lys Thr Ile Ser Lys Ala
    270                 275                 280 aaa ggg cag ccc cga gaa cca cag gtg tac acc ctg ccc cca tcc cgg      916
Lys Gly Gln Pro Arg Glu Pro Gln Val Tyr Thr Leu Pro Pro Ser Arg
285                 290                 295                 300 gat gag ctg acc aag aac cag gtc agc ctg acc tgc ctg gtc aaa ggc      964
Asp Glu Leu Thr Lys Asn Gln Val Ser Leu Thr Cys Leu Val Lys Gly
                305                 310                 315 ttc tat ccc agc gac atc gcc gtg gag tgg gag agc aat ggg cag ccg     1012
Phe Tyr Pro Ser Asp Ile Ala Val Glu Trp Glu Ser Asn Gly Gln Pro
            320                 325                 330 gag aac aac tac aag acc acg cct ccc gtg ctg gac tcc gac ggc tcc     1060
Glu Asn Asn Tyr Lys Thr Thr Pro Pro Val Leu Asp Ser Asp Gly Ser
        335                 340                 345 ttc ttc ctc tac agc aag ctc acc gtg gac aag agc agg tgg cag cag     1108
Phe Phe Leu Tyr Ser Lys Leu Thr Val Asp Lys Ser Arg Trp Gln Gln
    350                 355                 360 ggg aac gtc ttc tca tgc tcc gtg atg cat gag gct ctg cac aac cac     1156
Gly Asn Val Phe Ser Cys Ser Val Met His Glu Ala Leu His Asn His
365                 370                 375                 380 tac acg cag aag agc ctc tcc ctg tct ccg ggt aaa taatctagag          1202
Tyr Thr Gln Lys Ser Leu Ser Leu Ser Pro Gly Lys
                385                 390 gcgcgccaat ta                                                        1214

<210> SEQ ID NO 19
<211> LENGTH: 392
<212> TYPE: PRT
<213> ORGANISM: Artificial Sequence
<220> FEATURE:
<223> OTHER INFORMATION: TACI-Fc fusion protein

<400> SEQUENCE: 19

Met Asp Ala Met Lys Arg Gly Leu Cys Cys Val Leu Leu Leu Cys Gly
  1               5                  10                  15

Ala Val Phe Val Ser Leu Ser Gln Glu Ile His Ala Glu Leu Arg Arg
             20                  25                  30

Phe Arg Arg Ala Met Arg Ser Cys Pro Glu Glu Gln Tyr Trp Asp Pro
         35                  40                  45

Leu Leu Gly Thr Cys Met Ser Cys Lys Thr Ile Cys Asn His Gln Ser
     50                  55                  60

Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
                 85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Arg Gln Arg
        115                 120                 125

Ser Gly Glu Val Glu Asn Asn Ser Asp Asn Ser Gly Arg Tyr Gln Gly
    130                 135                 140

Leu Glu His Arg Gly Ser Glu Ala Ser Pro Ala Leu Pro Gly Leu Lys
145                 150                 155                 160
```

-continued

```
Glu Pro Lys Ser Ser Asp Lys Thr His Thr Cys Pro Pro Cys Pro Ala
                165                 170                 175
Pro Glu Ala Glu Gly Ala Pro Ser Val Phe Leu Phe Pro Pro Lys Pro
            180                 185                 190
Lys Asp Thr Leu Met Ile Ser Arg Thr Pro Glu Val Thr Cys Val Val
        195                 200                 205
Val Asp Val Ser His Glu Asp Pro Glu Val Lys Phe Asn Trp Tyr Val
    210                 215                 220
Asp Gly Val Glu Val His Asn Ala Lys Thr Lys Pro Arg Glu Glu Gln
225                 230                 235                 240
Tyr Asn Ser Thr Tyr Arg Val Val Ser Val Leu Thr Val Leu His Gln
                245                 250                 255
Asp Trp Leu Asn Gly Lys Glu Tyr Lys Cys Lys Val Ser Asn Lys Ala
            260                 265                 270
Leu Pro Ser Ser Ile Glu Lys Thr Ile Ser Lys Ala Lys Gly Gln Pro
        275                 280                 285
Arg Glu Pro Gln Val Tyr Thr Leu Pro Pro Ser Arg Asp Glu Leu Thr
    290                 295                 300
Lys Asn Gln Val Ser Leu Thr Cys Leu Val Lys Gly Phe Tyr Pro Ser
305                 310                 315                 320
Asp Ile Ala Val Glu Trp Glu Ser Asn Gly Gln Pro Glu Asn Asn Tyr
                325                 330                 335
Lys Thr Thr Pro Pro Val Leu Asp Ser Asp Gly Ser Phe Phe Leu Tyr
            340                 345                 350
Ser Lys Leu Thr Val Asp Lys Ser Arg Trp Gln Gln Gly Asn Val Phe
        355                 360                 365
Ser Cys Ser Val Met His Glu Ala Leu His Asn His Tyr Thr Gln Lys
    370                 375                 380
Ser Leu Ser Leu Ser Pro Gly Lys
385                 390

<210> SEQ ID NO 20
<211> LENGTH: 1070
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1048)

<400> SEQUENCE: 20
tattaggccg gccacc atg gat gca atg aag aga ggg ctc tgc tgt gtg ctg      52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc       100
Leu Leu Cys Gly Ala Val Phe Val Ser Leu Ser Gln Glu Ile His Ala
        15                  20                  25 gag ttg aga cgc ttc cgt aga gct atg aga tcc tgc ccc gaa gag cag       148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc       196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc       244
Asn His Gln Ser Gln Arg Thr Cys Ala Ala Phe Cys Arg Ser Leu Ser
                 65                  70                  75
```

| | | |
|---|---|---|
| tgc cgc aag gag caa ggc aag ttc tat gac cat ctc ctg agg gac tgc<br>Cys Arg Lys Glu Gln Gly Lys Phe Tyr Asp His Leu Leu Arg Asp Cys<br>80                     85                  90 | | 292 |
| atc agc tgt gcc tcc atc tgt gga cag cac cct aag caa tgt gca tac<br>Ile Ser Cys Ala Ser Ile Cys Gly Gln His Pro Lys Gln Cys Ala Tyr<br>95                 100               105 | | 340 |
| ttc tgt gag aac gag ccc aaa tct tca gac aaa act cac aca tgc cca<br>Phe Cys Glu Asn Glu Pro Lys Ser Ser Asp Lys Thr His Thr Cys Pro<br>110                 115               120 | | 388 |
| ccg tgc cca gca cct gaa gcc gag ggg gca ccg tca gtc ttc ctc ttc<br>Pro Cys Pro Ala Pro Glu Ala Glu Gly Ala Pro Ser Val Phe Leu Phe<br>125                 130               135               140 | | 436 |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>145                 150               155 | | 484 |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>160                 165               170 | | 532 |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>175                 180               185 | | 580 |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>190                 195               200 | | 628 |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>205                 210               215               220 | | 676 |
| tcc aac aaa gcc ctc cca tcc tcc atc gag aaa acc atc tcc aaa gcc<br>Ser Asn Lys Ala Leu Pro Ser Ser Ile Glu Lys Thr Ile Ser Lys Ala<br>225                 230               235 | | 724 |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>240                 245               250 | | 772 |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>255                 260               265 | | 820 |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>270                 275               280 | | 868 |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>285                 290               295               300 | | 916 |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>305                 310               315 | | 964 |
| ggg aac gtc ttc tca tgc tcc gtg atg cat gag gct ctg cac aac cac<br>Gly Asn Val Phe Ser Cys Ser Val Met His Glu Ala Leu His Asn His<br>320                 325               330 | | 1012 |
| tac acg cag aag agc ctc tcc ctg tct ccg ggt aaa taatctagag<br>Tyr Thr Gln Lys Ser Leu Ser Leu Ser Pro Gly Lys<br>335                 340 | | 1058 |
| gcgcgccaat ta | | 1070 |

<210> SEQ ID NO 21
<211> LENGTH: 344
<212> TYPE: PRT
<213> ORGANISM: Artificial Sequence
<220> FEATURE:
<223> OTHER INFORMATION: TACI-Fc fusion protein

<400> SEQUENCE: 21

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
             20                  25                  30

Phe Arg Arg Ala Met Arg Ser Cys Pro Glu Glu Gln Tyr Trp Asp Pro
         35                  40                  45

Leu Leu Gly Thr Cys Met Ser Cys Lys Thr Ile Cys Asn His Gln Ser
     50                  55                  60

Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
             85                  90                  95

Ser Ile Cys Gly Gln His Pro Lys Gln Cys Ala Tyr Phe Cys Glu Asn
         100                 105                 110

Glu Pro Lys Ser Ser Asp Lys Thr His Thr Cys Pro Pro Cys Pro Ala
     115                 120                 125

Pro Glu Ala Glu Gly Ala Pro Ser Val Phe Leu Phe Pro Pro Lys Pro
130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
             165                 170                 175

Asp Gly Val Glu Val His Asn Ala Lys Thr Lys Pro Arg Glu Glu Gln
         180                 185                 190

Tyr Asn Ser Thr Tyr Arg Val Val Ser Val Leu Thr Val Leu His Gln
     195                 200                 205

Asp Trp Leu Asn Gly Lys Glu Tyr Lys Cys Lys Val Ser Asn Lys Ala
210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
             245                 250                 255

Lys Asn Gln Val Ser Leu Thr Cys Leu Val Lys Gly Phe Tyr Pro Ser
         260                 265                 270

Asp Ile Ala Val Glu Trp Glu Ser Asn Gly Gln Pro Glu Asn Asn Tyr
     275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
             325                 330                 335

Ser Leu Ser Leu Ser Pro Gly Lys
         340
```

<210> SEQ ID NO 22
<211> LENGTH: 1082
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1060)

<400> SEQUENCE: 22

-continued

```
tattaggccg gccacc atg gat gca atg aag aga ggg ctc tgc tgt gtg ctg              52
                 Met Asp Ala Met Lys Arg Gly Leu Cys Cys Val Leu
                  1               5                  10 ctg ctg tgt ggc gcc gtc ttc gtt tcg ctc agc cag gaa atc cat gcc              100
Leu Leu Cys Gly Ala Val Phe Val Ser Leu Ser Gln Glu Ile His Ala
            15                  20                  25 gag ttg aga cgc ttc cgt aga gct atg aga tcc tgc ccc gaa gag cag              148
Glu Leu Arg Arg Phe Arg Arg Ala Met Arg Ser Cys Pro Glu Glu Gln
         30                  35                  40 tac tgg gat cct ctg ctg ggt acc tgc atg tcc tgc aaa acc att tgc              196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc              244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc              292
Cys Arg Lys Glu Gln Gly Lys Phe Tyr Asp His Leu Leu Arg Asp Cys
             80                  85                  90 atc agc tgt gcc tcc atc tgt gga cag cac cct aag caa tgt gca tac              340
Ile Ser Cys Ala Ser Ile Cys Gly Gln His Pro Lys Gln Cys Ala Tyr
         95                 100                 105 ttc tgt gag aac aag ctc agg agc gag ccc aaa tct tca gac aaa act              388
Phe Cys Glu Asn Lys Leu Arg Ser Glu Pro Lys Ser Ser Asp Lys Thr
     110                 115                 120 cac aca tgc cca ccg tgc cca gca cct gaa gcc gag ggg gca ccg tca              436
His Thr Cys Pro Pro Cys Pro Ala Pro Glu Ala Glu Gly Ala Pro Ser
125                 130                 135                 140 gtc ttc ctc ttc ccc cca aaa ccc aag gac acc ctc atg atc tcc cgg              484
Val Phe Leu Phe Pro Pro Lys Pro Lys Asp Thr Leu Met Ile Ser Arg
                145                 150                 155 acc cct gag gtc aca tgc gtg gtg gtg gac gtg agc cac gaa gac cct              532
Thr Pro Glu Val Thr Cys Val Val Val Asp Val Ser His Glu Asp Pro
            160                 165                 170 gag gtc aag ttc aac tgg tac gtg gac ggc gtg gag gtg cat aat gcc              580
Glu Val Lys Phe Asn Trp Tyr Val Asp Gly Val Glu Val His Asn Ala
        175                 180                 185 aag aca aag ccg cgg gag gag cag tac aac agc acg tac cgt gtg gtc              628
Lys Thr Lys Pro Arg Glu Glu Gln Tyr Asn Ser Thr Tyr Arg Val Val
190                 195                 200 agc gtc ctc acc gtc ctg cac cag gac tgg ctg aat ggc aag gag tac              676
Ser Val Leu Thr Val Leu His Gln Asp Trp Leu Asn Gly Lys Glu Tyr
205                 210                 215                 220 aag tgc aag gtc tcc aac aaa gcc ctc cca tcc tcc atc gag aaa acc              724
Lys Cys Lys Val Ser Asn Lys Ala Leu Pro Ser Ser Ile Glu Lys Thr
                225                 230                 235 atc tcc aaa gcc aaa ggg cag ccc cga gaa cca cag gtg tac acc ctg              772
Ile Ser Lys Ala Lys Gly Gln Pro Arg Glu Pro Gln Val Tyr Thr Leu
            240                 245                 250 ccc cca tcc cgg gat gag ctg acc aag aac cag gtc agc ctg acc tgc              820
Pro Pro Ser Arg Asp Glu Leu Thr Lys Asn Gln Val Ser Leu Thr Cys
        255                 260                 265 ctg gtc aaa ggc ttc tat ccc agc gac atc gcc gtg gag tgg gag agc              868
Leu Val Lys Gly Phe Tyr Pro Ser Asp Ile Ala Val Glu Trp Glu Ser
    270                 275                 280 aat ggg cag ccg gag aac aac tac aag acc acg cct ccc gtg ctg gac              916
Asn Gly Gln Pro Glu Asn Asn Tyr Lys Thr Thr Pro Pro Val Leu Asp
285                 290                 295                 300 tcc gac ggc tcc ttc ttc ctc tac agc aag ctc acc gtg gac aag agc              964
Ser Asp Gly Ser Phe Phe Leu Tyr Ser Lys Leu Thr Val Asp Lys Ser
```

```
              305                 310                 315
agg tgg cag cag ggg aac gtc ttc tca tgc tcc gtg atg cat gag gct      1012
Arg Trp Gln Gln Gly Asn Val Phe Ser Cys Ser Val Met His Glu Ala
            320                 325                 330 ctg cac aac cac tac acg cag aag agc ctc tcc ctg tct ccg ggt aaa      1060
Leu His Asn His Tyr Thr Gln Lys Ser Leu Ser Leu Ser Pro Gly Lys
        335                 340                 345 taatctagag gcgcgccaat ta                                             1082

<210> SEQ ID NO 23
<211> LENGTH: 348
<212> TYPE: PRT
<213> ORGANISM: Artificial Sequence
<220> FEATURE:
<223> OTHER INFORMATION: TACI-Fc fusion protein

<400> SEQUENCE: 23

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
                20                  25                  30

Phe Arg Arg Ala Met Arg Ser Cys Pro Glu Glu Gln Tyr Trp Asp Pro
            35                  40                  45

Leu Leu Gly Thr Cys Met Ser Cys Lys Thr Ile Cys Asn His Gln Ser
        50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300
```

```
Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 24
<211> LENGTH: 1109
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1090)

<400> SEQUENCE: 24
tattaggccg gccacc atg gat gca atg aag aga ggg ctc tgc tgt gtg ctg     52
                Met Asp Ala Met Lys Arg Gly Leu Cys Cys Val Leu
                1               5                   10 ctg ctg tgt ggc gcc gtc ttc gtt tcg ctc agc cag gaa atc cat gcc      100
Leu Leu Cys Gly Ala Val Phe Val Ser Leu Ser Gln Glu Ile His Ala
        15                  20                  25 gag ttg aga cgc ttc cgt aga gct atg aga tcc tgc ccc gaa gag cag      148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc      196
Tyr Trp Asp Pro Leu Leu Gly Thr Cys Met Ser Cys Lys Thr Ile Cys
45                  50                  55                  60 aac cat cag agc cag cgc acc tgt gca gcc ttc tgc agg tca ctc agc      244
Asn His Gln Ser Gln Arg Thr Cys Ala Ala Phe Cys Arg Ser Leu Ser
                65                  70                  75 tgc cgc aag gag caa ggc aag ttc tat gac cat ctc ctg agg gac tgc      292
Cys Arg Lys Glu Gln Gly Lys Phe Tyr Asp His Leu Leu Arg Asp Cys
            80                  85                  90 atc agc tgt gcc tcc atc tgt gga cag cac cct aag caa tgt gca tac      340
Ile Ser Cys Ala Ser Ile Cys Gly Gln His Pro Lys Gln Cys Ala Tyr
        95                  100                 105 ttc tgt gag aac aag ctc agg agc cca gtg aac ctt cca cca gag ctc      388
Phe Cys Glu Asn Lys Leu Arg Ser Pro Val Asn Leu Pro Pro Glu Leu
    110                 115                 120 agg gag ccc aaa tct tca gac aaa act cac aca tgc cca ccg tgc cca      436
Arg Glu Pro Lys Ser Ser Asp Lys Thr His Thr Cys Pro Pro Cys Pro
125                 130                 135                 140 gca cct gaa gcc gag ggg gca ccg tca gtc ttc ctc ttc ccc cca aaa      484
Ala Pro Glu Ala Glu Gly Ala Pro Ser Val Phe Leu Phe Pro Pro Lys
                145                 150                 155 ccc aag gac acc ctc atg atc tcc cgg acc cct gag gtc aca tgc gtg      532
Pro Lys Asp Thr Leu Met Ile Ser Arg Thr Pro Glu Val Thr Cys Val
            160                 165                 170 gtg gtg gac gtg agc cac gaa gac cct gag gtc aag ttc aac tgg tac      580
Val Val Asp Val Ser His Glu Asp Pro Glu Val Lys Phe Asn Trp Tyr
        175                 180                 185 gtg gac ggc gtg gag gtg cat aat gcc aag aca aag ccg cgg gag gag      628
Val Asp Gly Val Glu Val His Asn Ala Lys Thr Lys Pro Arg Glu Glu
    190                 195                 200 cag tac aac agc acg tac cgt gtg gtc agc gtc ctc acc gtc ctg cac      676
Gln Tyr Asn Ser Thr Tyr Arg Val Val Ser Val Leu Thr Val Leu His
205                 210                 215                 220 cag gac tgg ctg aat ggc aag gag tac aag tgc aag gtc tcc aac aaa      724
```

-continued

```
Gln Asp Trp Leu Asn Gly Lys Glu Tyr Lys Cys Lys Val Ser Asn Lys
                225                 230                 235 gcc ctc cca tcc tcc atc gag aaa acc atc tcc aaa gcc aaa ggg cag        772
Ala Leu Pro Ser Ser Ile Glu Lys Thr Ile Ser Lys Ala Lys Gly Gln
                240                 245                 250 ccc cga gaa cca cag gtg tac acc ctg ccc cca tcc cgg gat gag ctg        820
Pro Arg Glu Pro Gln Val Tyr Thr Leu Pro Pro Ser Arg Asp Glu Leu
            255                 260                 265 acc aag aac cag gtc agc ctg acc tgc ctg gtc aaa ggc ttc tat ccc        868
Thr Lys Asn Gln Val Ser Leu Thr Cys Leu Val Lys Gly Phe Tyr Pro
        270                 275                 280 agc gac atc gcc gtg gag tgg gag agc aat ggg cag ccg gag aac aac        916
Ser Asp Ile Ala Val Glu Trp Glu Ser Asn Gly Gln Pro Glu Asn Asn
285                 290                 295                 300 tac aag acc acg cct ccc gtg ctg gac tcc gac ggc tcc ttc ttc ctc        964
Tyr Lys Thr Thr Pro Pro Val Leu Asp Ser Asp Gly Ser Phe Phe Leu
                305                 310                 315 tac agc aag ctc acc gtg gac aag agc agg tgg cag cag ggg aac gtc       1012
Tyr Ser Lys Leu Thr Val Asp Lys Ser Arg Trp Gln Gln Gly Asn Val
                320                 325                 330 ttc tca tgc tcc gtg atg cat gag gct ctg cac aac cac tac acg cag       1060
Phe Ser Cys Ser Val Met His Glu Ala Leu His Asn His Tyr Thr Gln
            335                 340                 345 aag agc ctc tcc ctg tct ccg ggt aaa taa tctagaggcg cgccaatta          1109
Lys Ser Leu Ser Leu Ser Pro Gly Lys *
        350                 355

<210> SEQ ID NO 25
<211> LENGTH: 357
<212> TYPE: PRT
<213> ORGANISM: Artificial Sequence
<220> FEATURE:
<223> OTHER INFORMATION: TACI-Fc fusion protein

<400> SEQUENCE: 25

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Glu Pro Lys
        115                 120                 125

Ser Ser Asp Lys Thr His Thr Cys Pro Pro Cys Pro Ala Pro Glu Ala
    130                 135                 140

Glu Gly Ala Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
```

```
                180                 185                 190
Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
        210                 215                 220

Asn Gly Lys Glu Tyr Lys Cys Lys Val Ser Asn Lys Ala Leu Pro Ser
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 26
<211> LENGTH: 311
<212> TYPE: PRT
<213> ORGANISM: Artificial Sequence
<220> FEATURE:
<223> OTHER INFORMATION: BAFF-R-Fc fusion protein

<400> SEQUENCE: 26

Met Ser Ala Leu Leu Ile Leu Ala Leu Val Gly Ala Ala Val Ala Ser
1               5                   10                  15

Thr Arg Arg Gly Pro Arg Ser Leu Arg Gly Arg Asp Ala Pro Ala Pro
            20                  25                  30

Thr Pro Cys Val Pro Ala Glu Cys Phe Asp Leu Leu Val Arg His Cys
        35                  40                  45

Val Ala Cys Gly Leu Leu Arg Thr Pro Arg Pro Lys Pro Ala Gly Ala
    50                  55                  60

Ser Ser Pro Ala Pro Arg Thr Ala Leu Gln Pro Gln Glu Ser Gln Val
65                  70                  75                  80

Thr Asp Lys Ala Ala His Tyr Thr Leu Cys Pro Pro Cys Pro Ala Pro
                85                  90                  95

Glu Leu Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Ala Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
```

-continued

```
            180                 185                 190
Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Glu Glu Met Thr Lys
        210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Lys Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
        290                 295                 300

Leu Ser Leu Ser Pro Gly Lys
305                 310
```

LEVELS OF BCMA PROTEIN EXPRESSION ON B CELLS AND USE IN METHODS OF TREATING SYSTEMIC LUPUS ERYTHEMATOSUS

CROSS-REFERENCE TO RELATED APPLICATIONS

This application is a divisional of U.S. application Ser. No. 12/429,502, filed Apr. 24, 2009, which claims the benefit of U.S. Provisional Application No. 61/047,869 filed Apr. 25, 2008, each of which are herein incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 442957seqlist.txt, a creation date of Feb. 27, 2014, and a size of 66.7 KB. The sequence listing filed via EFS-Web is part of the specification and is hereby incorporated in its entirety by reference herein.

BACKGROUND OF THE INVENTION

Cellular interactions which occur during an immune response are regulated by members of several families of cell surface receptors, including the tumor necrosis factor receptor (TNFR) family. The TNFR family consists of a number of integral membrane glycoprotein receptors many of which, in conjunction with their respective ligands, regulate interactions between different hematopoietic cell lineages (Smith et al., *The TNF Receptor Superfamily of Cellular and Viral Proteins: Activation, Costimulation and Death*, 76:959-62, 1994; Cosman, *Stem Cells* 12:440-55, 1994).

One such receptor is BCMA, a nonglycosylated integral membrane type I protein that is preferentially expressed in mature B lymphocytes (Gras et al., *Int. Immunol.* 17:1093-106, 1995). BCMA is located on the cell surface, as well as in a perinulear Golgi-like structure. Overexpression of BCMA in 293 cells activates NF-kappa B, Elk-1, the c-Jun N-terminal kinase, and the p38 mitogen-activated protein kinase, thus producing signals for cell survival and proliferation (Hatzoglou et al., *J. Immunol.*, 165: 1322-30, 2000). Another such receptor is TACI, transmembrane activator and CAML-interactor (von Bülow and Bram, *Science* 228: 138-41, 1997 and WIPO Publication WO 98/39361). TACI is a membrane bound receptor having an extracellular domain containing two cysteine-rich pseudo-repeats, a transmembrane domain and a cytoplasmic domain that interacts with CAML (calcium-modulator and cyclophilin ligand), an integral membrane protein located at intracellular vesicles which is a co-inducer of NF-AT activation when overexpressed in Jurkat cells. A third receptor from the TNFR family expressed on the surface of B cells is BAFF-R (Thompson et al., *Science*, 293: 2108-11, 2001. Signaling of this receptor, also known as BAFF/BLyS receptor 3 (BR3), promotes processing of the transcription factor NF-kappaB2/p100 to p52. This cascade is physiologically relevant for survival of B cells, and therefore, the progression of B cells to maturation (Claudio et al., *Nat. Immunol.*, 3: 898-9, 2002; Kayagaki et al., *Immunity*, 17: 515-24, 2002).

A number of BLyS and/or APRIL antagonists have been developed in order to block the binding of these ligands to the receptor members of the family, in order to block results of this binding which include but should not be limited to B cell costimulation, plasmablast and plasma cell survival, Ig class switching, enhanced B-cell antigen presenting cell function, survival of malignant B cells, development of B-1 cell function, B cell development beyond the T-1 stage, and complete germinal centre formation. Some of these molecules can also bind to and block the effect of APRIL on B cells and other components of the immune system (Dillon et al. (2006) Nat. Rev. Drug Dis. 5, 235-246). Molecules that have been developed to affect B cell function by interfering with BLyS and/or APRIL binding include BLyS antibodies such as Lymphostat-B (Belimumab) (Baker et al, (2003) Arthritis Rheum, 48, 3253-3265 and WO 02/02641); receptor-extracellular domain/Fc domain fusions proteins such as TACI-Ig, including one particular embodiment, atacicept (U.S. Patent Application No. 20060034852), BAFF-R-Fc (WO 05/0000351), and BCMA-Ig or other fusion proteins utilizing receptor extracellular domains. A further class of BLyS and/or APRIL antagonists include other molecules relying on BLyS binding ability to block binding to its receptors such as AMG 623, receptor antibodies, and other molecules disclosed in WO 03/035846 and WO 02/16312.

There remains a need in the art for further identification of cell surface expression patterns of these TNFR family members that are statistically associated with autoimmune disease, such as systemic lupus erythromatosus (SLE). Such information is important for identifying individuals who have a propensity toward developing such autoimmune diseases, are in an active disease state, and for identifying those that will respond favorably to BLyS and/or APRIL antagonist treatment of these diseases. The present invention addresses this need by providing a cell surface expression pattern associated with autoimmune diseases and providing diagnostic tests determining the presence of this expression pattern, namely increased BCMA expression on B cells for those suffering from autoimmune disease as compared to healthy controls.

SUMMARY OF THE INVENTION

The present invention provides a method of screening for levels of TNFR family members on the B cell surface. As it has been shown that elevated levels of BCMA are significantly associated with autoimmune disease, such as SLE, this measurement is useful as a diagnostic assay. Such diagnostic assays are useful in predicting an individual's likelihood of having a condition associated with autoimmune activity, such as SLE. The invention further provides methods for determining appropriate treatment for an individual with an autoimmune disease, such as SLE.

Detection of high levels of BCMA on B cells of patients exhibiting autoimmune activity, such as those diagnosed with SLE, allows selection of a treatment plan that is most likely to be effective in treating the condition. These treatment plans generally involve the use of BLyS antagonists, either singly or in combination with another pharmaceutical such as an immune suppressive drug (like MMF or Cellcept®) or a CD 20 antagonist (like Rituxan®).

Thus, the invention further provides methods for treating an individual clinically diagnosed with an autoimmune condition, generally comprising detecting high levels of BCMA on cells, as compared to levels seen on B cells of healthy controls, and selecting a treatment plan that is most effective for individuals clinically diagnosed with an autoimmune disease. Detection of high levels of BCMA on B cells also allows one to predict a patient's likelihood to respond to a specific drug treatment, particularly BLyS and/or APRIL antagonists. Thus, the invention further provides methods of predicting a patient's likelihood to respond to BLyS and/or APRIL antagonists (either singly or in combination with other drugs) during treatment for an autoimmune condition, such as SLE.

Very specifically, the present invention describes a method of detecting increased BCMA protein expression on the surface of B cells of an individual comprising measuring a first level of BCMA protein expression in a biological sample and comparing that level to a second level of BCMA protein expression present on the surface of B cells of a healthy individual and determining the first level is increased as compared to the second level, wherein said increased BCMA protein expression is associated with an autoimmune disease. The autoimmune disease in the present invention can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

The present invention also describes a method of treating an individual clinically diagnosed with an autoimmune disease, comprising analyzing a biological sample from an individual clinically diagnosed with autoimmune disease for the presence or absence of elevated BCMA protein expression levels on their B cells, wherein the presence of elevated BCMA protein expression levels is associated with the clinical diagnosis of autoimmune disease; and selecting a treatment plan that is most effective for individuals clinically diagnosed as having a condition associated with an increased BCMA protein expression level. The treatment plan can involve administration of a BLyS antagonist. And said BLyS antagonist can also be an APRIL antagonist. For this method the autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

Furthermore, the present invention describes methods for predicting a patient's likelihood to respond to a drug treatment for an autoimmune disease, comprising determining the level of BCMA protein expression on the patient's B cells, wherein the presence of elevated BCMA protein expression levels is predictive of the patient's likelihood to respond to a drug treatment for the condition. The autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE. Additionally, the present invention method can include a drug treatment involves administration of a BLyS antagonist and said BLyS antagonist can also be an APRIL antagonist.

The present invention also encompasses an in vitro method of detecting increased BCMA protein expression on the surface of B cells of an individual, comprising measuring the level of BCMA protein expression on the surface of B cells in a test biological sample from the individual; comparing that level to the level of BCMA protein expression on the surface of B cells in a sample from a healthy control; and determining whether the level of BCMA protein expression on the surface is B cells in the test biological sample is increased as compared to the level in the control sample; wherein said increased BCMA protein expression is associated with an autoimmune disease. The autoimmune disease in this method can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

In a further embodiment, the present invention includes an in vitro method of selecting a treatment plan that is most effective for treating an individual clinically diagnosed with an autoimmune disease, comprising analyzing in vitro a biological sample from an individual clinically diagnosed with autoimmune disease for the presence or absence of elevated BCMA levels on their B cells, wherein the presence of elevated BCMA levels is associated with the clinical diagnosis of autoimmune disease. For this method, the treatment plan can involves the use of a BLyS antagonist and the BLyS antagonist can also be an APRIL antagonist. The autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis.

In particular, the autoimmune disease is SLE.

In a still further embodiment, the present invention includes an in vitro method for predicting a patient's likelihood to respond to a drug treatment for an autoimmune disease, comprising determining the level of BCMA expression on the surface of B cells in a sample from the patient; wherein the presence of elevated B cell levels is predictive of the patient's likelihood to respond to a drug treatment for the condition. The autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE. The drug treatment of the present invention can comprise a BLyS antagonist and said BLyS antagonist can also be an APRIL antagonist.

Finally, the present invention contemplates a BLys antagonist for use in the treatment of an autoimmune disease in a patient, wherein said patient has elevated levels of BCMA expression on B cells. The antagonist can be a BLyS antibody, such as Lymphostat-B. The antagonist can also be a receptor-extracellular domain/Fc domain fusion protein selected from the group consisting of TACI-Ig, BCMA-Ig, and BAFF-R-Ig. In particular, the receptor-extracellular domain/Fc domain fusion protein can be TACI-Ig, such as atacicept.

These and other aspects of the invention will become apparent to those persons skilled the art upon reading the details of the invention as more fully described below.

BRIEF DESCRIPTION OF THE DRAWINGS

FIG. 2 lower level graphs the inverse relationship between serum IgG anti-dsDNA and the lack of correlation between serum BAFF (BCMA) and SLEDAI score (disease activity).

BRIEF DESCRIPTION OF THE INVENTION

Figure 1A:
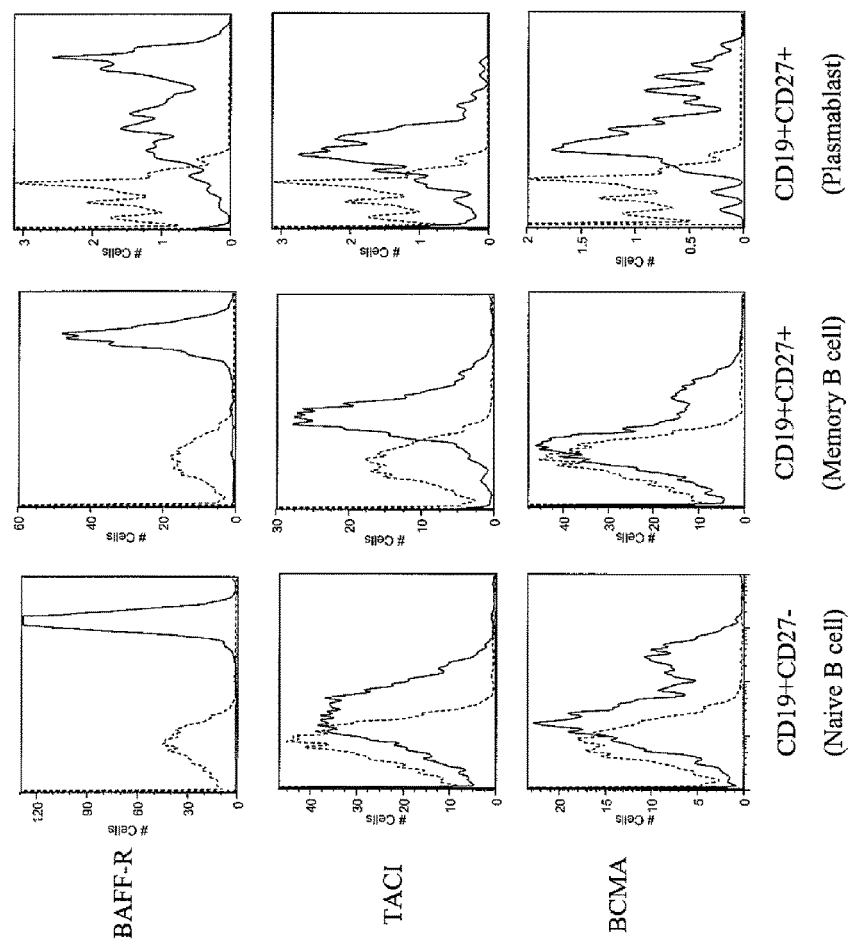
FIG. 1A shows the levels of BAFF-R, TACI, and BCMA present on the cells surface of naïve B cells, memory B cells, and plasmablasts.

The present invention provides a method for screening TNFR family members on the surface of B cells and the use of this information for predicting the presence of autoimmune disease and predicting the likelihood that a patient would respond to BLyS antagonist treatment. The invention is based on the finding that the levels of BCMA protein expression on the surface of B cells is elevated and BLyS antagonists selectively neutralize the production of IgG by said cells. This observation allows development of diagnostic assays to detect the presence of increased BCMA on the B cells surface where these higher levels are associated with autoimmune disease, such as SLE, and also may predict the likelihood that an individual will successfully respond to treatment methods that neutralize such B cells, i.e., BLyS and/or APRIL antagonists.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polymorphism includes a plurality of such polymorphisms, reference to "a nucleic acid molecule" includes a plurality of such nucleic acid molecules, and reference to "the method" includes reference to one or more methods, method steps, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein, the term "BCMA" is intended to generically refer to both the wild-type and variant forms of the gene sequence, unless specifically denoted otherwise. As it is commonly used in the art, the term "gene" is intended to refer to the genomic region encompassing 5' untranslated region(s) (UTR), exons, introns, and 3' UTR. Individual segments may be specifically referred to, e.g. promoter, coding region, etc. Combinations of such segments that provide for a complete BCMA protein may be referred to generically as a protein coding sequence. The nucleotide sequence of BCMA are publicly available (GenBank Accession number as BC058291). There are four major haplotypes of the BCMA gene in the human genome, in the present disclosure the term "BCMA" is meant to encompass all four (Kawasaki et al., Genes Immun. 2:276-9, 2001).

The term "polymorphism", as used herein, refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

In the broadest sense, as used herein, the terms "autoimmune disease," refer to a disease wherein a patient's immune system is producing an unwanted immune response to one or more of their own proteins. Representative examples of autoimmune diseases include rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as: where $[X^+]$ is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

Stringent conditions for both DNA/DNA and DNA/RNA hybridization are as described by Sambrook et al. Molecular Cloning, A Laboratory Manual, 2nd Ed., Cold Spring Harbor Laboratory Press, Cold Spring Harbor, N.Y., 1989, herein incorporated by reference. For example, see page 7.52 of Sambrook et al.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a "recombinant host cell".

The term "binds specifically," in the context of antibody binding, refers to high avidity and/or high affinity binding of an antibody to a specific polypeptide i.e., epitope of a polymorphic BCMA polypeptide. Antibody binding to an epitope on a specific polymorphic BCMA polypeptide (also referred to herein as "a polymorphic BCMA epitope") is preferably stronger than binding of the same antibody to any other epitope, particularly those which may be present in molecules in association with, or in the same sample, as the specific polypeptide of interest, e.g., binds more strongly to a specific BCMA polymorphic epitope than to a different BCMA epitope so that by adjusting binding conditions the antibody binds almost exclusively to the specific BCMA polymorphic epitope and not to any other BCMA epitope, and not to any other BCMA polypeptide which does not comprise the polymorphic epitope. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a specific BCMA polypeptide with a binding affinity of $10^7$ mole/l or more, preferably $10^8$ mole/l or more are said to bind specifically to the specific BCMA polypeptide. In general, an antibody with a binding affinity of $10^6$ mole/liters or less is not useful in that it will not bind an antigen at a detectable level using conventional methodology currently used.

The term "monoclonal antibody" as used herein refers to an antibody obtained from a population of substantially homogeneous antibodies, i. e., the individual antibodies comprising the population are identical except for possible naturally occurring mutations that can be present in minor amounts.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e. g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Methods of making chimeric antibodies are known in the art.

"Humanized" forms of non-human (e. g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin.

For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992). The humanized antibody includes a PRIMATIZED antibody wherein the antigen-binding region of the antibody is derived from an antibody produced by, e. g., immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1): 86-95 (1991).

"Functional fragments" of the binding antibodies of the invention are those fragments that retain binding to BLyS, TACI, BAFF-R, or BCMA with substantially the same affinity as the intact full chain molecule from which they are derived and may be able to deplete B cells as measured by in vitro or in vivo assays such as those described herein.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e. g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e. g. Natural Killer (NK) cells, neutrophils, and macrophages) enable these cytotoxic effector cells to bind specifically to an antigen-bearing-target cell and subsequently kill the-target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Ann. Rev. Immunol 9: 457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e. g., in a animal model such as that disclosed in Clynes et al. PNAS (USA) 95: 652-656 (1998).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e. g. as described in Gazzano-Santoro etal., J. Immunol. Methods 202: 163 (1996), may be performed.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "detectably labeled antibody" refers to an antibody (or antibody fragment which retains binding specificity for a BCMA polypeptide or epitope), having an attached detectable label. The detectable label is normally attached by-chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)).

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

"Immunosuppressive drugs" are any molecules that interfere with the immune system and blunt its response to foreign or self antigens. Cyclophosphamide (CYC) and mycophenolate mofetil (MMF) are two such kinds of molecules. This term is intended to encompass any drug or molecule useful as a therapeutic agent in downregulating the immune system.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

A "conjugate" refers to any hybrid molecule, including fusion proteins and as well as molecules that contain both amino acid or protein portions and non-protein portions. Conjugates may be synthesized by a variety of techniques known in the art including, for example, recombinant DNA techniques, solid phase synthesis, solution phase synthesis, organic chemical synthetic techniques or a combination of these techniques. The choice of synthesis will depend upon the particular molecule to be generated. For example, a hybrid molecule not entirely "protein" in nature may be synthesized by a combination of recombinant techniques and solution phase techniques.

As used herein, the term "Fc-fusion protein" designates antibody-like molecules which combine the binding specificity of a heterologous protein with the effector functions of immunoglobulin constant domains. Structurally, the Fc-fusion proteins comprise a fusion of an amino acid sequence with the desired binding specificity which is other than the antigen recognition and binding site of an antibody (i. e., is "heterologous"), and an immunoglobulin constant domain sequence. The Fc-fusion protein molecule typically includes a contiguous amino acid sequence comprising at least the binding site of a receptor or a ligand. The immunoglobulin constant domain sequence in the Fc-fusion protein can be obtained from any immunoglobulin, such as IgG-1, IgG-2, IgG-3, or IgG-4 subtypes, IgA (including IgA-1 and IgA-2), IgE, IgD or IgM. For example, useful Fc-fusion proteins according to this invention are polypeptides that comprise the BLyS binding portions of a BLyS receptor without the transmembrane or cytoplasmic sequences of the BLyS receptor. In one embodiment, the extracellular domain of BAFF-R, TACI or BCMA is fused to a constant domain of an immunoglobulin sequence.

The terms "individual," "subject," and "patient," used interchangeably herein, refer to a mammal, including, but not limited to, murines, simians, humans, mammalian farm animals, mammalian sport animals, and mammalian pets.

The term "mammal" refers to any animal classified as a mammal, including humans, domestic and farm animals, and zoo, sports, or pet animals, such as dogs, horses, cats, cows, etc. Preferably, the mammal herein is human.

Detection of BCMA Polypeptides

The present invention provides for detection of BCMA polypeptides. The term "BCMA polypeptide" encompasses an amino acid sequence encoded by an open reading frame (ORF) of a known BCMA polynucleotide, including the full-length native polypeptide and fragments thereof, particularly biologically active fragments and/or fragments corresponding to functional domains, e.g. a region or domain having biological activity, etc.; antigenic fragments thereof, and including fusions of the subject polypeptides to other proteins or parts thereof. The amino acid sequences of BCMA polypeptides have been disclosed. (See e.g. Laabi et al., *Nucleic Acids Research* 22: 1147-1154, 1994; Laabi et al., *EMBO J.*, 11: 3897-3904 (1992); Gras et al., *Int. Immunology*, 7: 1093-1106 (1995); and Madry et al., *Int. Immunology*, 10: 1693-1702 (1998). The BCMA polypeptides of the invention can be isolated from a variety of sources, such as from human tissue types or from another source, or prepared by recombinant and/or synthetic methods. A polymorphism in a BCMA polypeptide is generally defined relative to a reference sequence.

As used herein, "polymorphic BCMA polypeptide" refers to an amino acid sequence of a recombinant or non-recombinant polypeptide having an amino acid sequence of i) a native polymorphic BCMA polypeptide, ii) a fragment of a polymorphic BCMA polypeptide, iii) polypeptide analogs of a polymorphic BCMA polypeptide, iv) variants of a polymorphic BCMA polypeptide; v) an immunologically active fragment of a polymorphic BCMA polypeptide; and vi) fusion proteins comprising a polymorphic BCMA polypeptide. Polymorphic BCMA polypeptides of the invention can be obtained from a biological sample, or from any source whether natural, synthetic, semi-synthetic or recombinant.

The term "polymorphic BCMA polypeptide" or "BCMA polypeptide" encompasses a polypeptide comprising from at least about 5 amino acids, at least about 10 amino acids, at least about 15 amino acids, at least about 25 amino acids, at least about 50 amino acids, at least about 75 amino acids, at least about 100 amino acids, at least about 200 amino acids, at least about 300 amino acids, at least about 400 amino acids, or up to the entire polypeptide of a polymorphic BCMA polypeptide. In some embodiments, a polymorphic BCMA polypeptide exhibits biological activity, e.g., the polypeptide causes proliferation of B-cells and production of immunoglobulin in an in vitro assay. Other assays for BCMA biological activity are known in the art and can be used to determine whether a polymorphic BCMA polypeptide exhibits biological activity and, if desired, to quantitate BCMA biological activity. BCMA biological assays are described in various publications, e.g., Moore et al., supra.

BCMA polypeptides can be obtained by any known method, or a combination of such methods, including isolation from natural sources; production by chemical synthesis; and production by standard recombinant techniques. BCMA polypeptides can be isolated from a biological source, using affinity chromatography, e.g., using antibodies specific for a BCMA polypeptide are immobilized on a solid support. The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, CHO cells, HEK293 cells, and the like, may be used as the expression host cells. In some situations, it is desirable to express the gene in eukaryotic cells, where the protein will benefit from native folding and post-translational modifications. The polypeptide can then be isolated from cell culture supernatant or from cell lysates using affinity chromatography methods or anion exchange/size exclusion chromatography methods, as described above.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The isolated proteins can be used to produce antibodies, which are in turn, used to detect the presence of that protein using standard assay systems, e.g., ELISA or FACS analysis.

Preparation of BCMA Polypeptides

In addition to the plurality of uses described in greater detail in following sections, the BCMA nucleic acid compositions are used in the preparation of all or a portion of the BCMA polypeptides, as described above. The polynucleotides (including cDNA or the full-length gene) are used to express a partial or complete gene product. Constructs comprising the subject polynucleotides can be generated synthetically. Alternatively, single-step assembly of a gene and entire plasmid from large numbers of oligodeoxyribonucleotides is described by, e.g., Stemmer et al., Gene (Amsterdam) (1995) 164(1):49-53. In this method, assembly PCR (the synthesis of long DNA sequences from large numbers of oligodeoxyribonucleotides (oligos)) is described. The method is derived from DNA shuffling (Stemmer, Nature (1994) 370:389-391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., Molecular Cloning: A Laboratory Manual, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a BCMA polypeptide-encoding polynucleotide is linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the BCMA gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

BCMA polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, HEK 293, CHO, *Xenopus* Oocytes, etc., may be used as the expression host cells. In some situations, it is desirable to express a polymorphic BCMA nucleic acid molecule in eukaryotic cells, where the polymorphic BCMA protein will benefit from native folding and post-translational modifications. Small peptides can also be synthesized in the laboratory. Polypeptides that are subsets of the complete BCMA sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., Nature (1978) 275:615; Goeddel et al., Nature (1979) 281:544; Goeddel et al., Nucleic Acids Res. (1980) 8:4057; EP 0 036,776; U.S. Pat. No. 4,551,433; DeBoer et al., Proc. Natl. Acad. Sci. (USA) (1983) 80:21-25; and Siebenlist et al., Cell (1980) 20:269.

Yeast. Expression systems in yeast include those described in Hinnen et al., Proc. Natl. Acad. Sci. (USA) (1978) 75:1929; Ito et al., J. Bacteriol. (1983) 153:163; Kurtz et al., Mol. Cell. Biol. (1986) 6:142; Kunze et al., J. Basic Microbiol. (1985)25:141; Gleeson et al., J. Gen.

Microbiol. (1986) 132:3459; Roggenkamp et al., Mol. Gen. Genet. (1986) 202:302; Das et al., J. Bacteriol. (1984) 158:1165; De Louvencourt et al., J. Bacteriol. (1983) 154: 737; Van den Berg et al., Bio/Technology (1990)8:135; Kunze et al., J. Basic Microbiol. (1985)25:141; Cregg et al., Mol. Cell. Biol. (1985) 5:3376; U.S. Pat. Nos. 4,837,148 and 4,929,555; Beach and Nurse, Nature (1981) 300:706; Davidow et al., Curr. Genet. (1985) 10:380; Gaillardin et al., Curr. Genet. (1985) 10:49; Ballance et al., Biochem. Biophys. Res. Commun. (1983) 112:284-289; Tilburn et al., Gene (1983) 26:205-221; Yelton et al., Proc. Natl. Acad. Sci. (USA) (1984) 81:1470-1474; Kelly and Hynes, EMBO J. (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: The Molecular Biology Of Baculoviruses (1986) (W. Doerfler, ed.); EP 0 127,839; EP 0 155,476; and Vlak et al., J. Gen. Virol. (1988) 69:765-776; Miller et al., Ann. Rev. Microbiol. (1988) 42:177; Carbonell et al., Gene (1988) 73:409; Maeda et al., Nature (1985) 315:592-594; Lebacq-Verheyden et al., Mol. Cell. Biol. (1988) 8:3129; Smith et al., Proc. Natl. Acad. Sci. (USA) (1985) 82:8844; Miyajima et al., Gene (1987) 58:273; and Martin et al., DNA (1988) 7:99. Numerous baculoviral strains and variants and corresponding permissive insect host cells from hosts are described in Luckow et al., Bio/Technology (1988) 6:47-55, Miller et al., Generic Engineering (1986) 8:277-279, and Maeda et al., Nature (1985) 315:592-594.

Mammalian Cells. Mammalian expression is accomplished as described in Dijkema et al., EMBO J. (1985) 4:761, Gorman et al., Proc. Natl. Acad. Sci. (USA) (1982) 79:6777, Boshart et al., Cell (1985) 41:521 and U.S. Pat. No. 4,399,216. Other features of mammalian expression are facilitated as described in Ham and Wallace, Meth. Enz. (1979) 58:44, Barnes and Sato, Anal. Biochem. (1980) 102:255, U.S. Pat. Nos. 4,767,704, 4,657,866, 4,927,762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated-in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of BCMA proteins without manipulation of the encoding nucleic acid itself, but instead through integration of a regulatory sequence into the genome of cell that already includes a gene encoding the desired protein, as described in the above incorporated patent documents.

Preparation of Antibodies Specific for BCMA Polypeptides

The invention further can encompass the use of antibodies, particularly isolated antibodies, that are specific for BCMA polypeptides. The antibodies of the invention are useful in a variety of diagnostic assays or treatments, as described in further detail below. For example, an antibody can be used to detect and/or measure the levels of a BCMA polypeptide in a biological sample.

Isolated BCMA polypeptides of the invention are useful for the production of antibodies, where short fragments provide for antibodies specific for the particular polypeptide, and larger fragments or the entire protein allow for the production of antibodies over the surface of the polypeptide. Accordingly, the methods of the present invention can utilize isolated antibodies which specifically bind a BCMA polypeptide, or antigenic fragment thereof. Antibodies may be raised to the wild-type or variant forms. Antibodies may be raised to isolated peptides corresponding to these domains, or to the native protein. Antibodies may be raised to polypeptides and/or peptide fragments of BCMA from any mammalian species. As one non-limiting example, an enzyme-linked immunosorbent assay (ELISA) can be used to determine the specificity of a given monoclonal antibody for a BCMA polypeptide.

The BCMA polypeptides are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, fusion proteins comprising such antibody fragments, detectably labeled antibodies, and chimeric antibodies. "Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies for a BCMA polypeptide. In specific embodiments, the BCMA antibody binds to the extracellular domain of BCMA. See, for example, Carter et al. (2007) Mol Can Ther 6:3009-18. In still further embodiments, the BCMA antibody binds to the extracellular domain of BCMA and further blocks BCMA activity. Methods for determining if a BCMA antibody blocks BCMA activity are known.

Antibodies are prepared in accordance with conventional ways, where the expressed is polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Antibodies may be attached, directly or indirectly (e.g., via a linker molecule) to a solid support for use in a diagnostic assay to determine and/or measure the presence of BCMA polypeptide in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an ELISA or radioimmunoassay (RIA), and the like); sheets, e.g., nylon, nitrocellulose, and the like; and chips, e.g., $SiO_2$ chips such as those used in microarrays. Accordingly, the invention further provides assay devices comprising antibodies attached to a solid support.

A single antibody or a battery of different antibodies can then be used to create an assay device. Such an assay device can be prepared using conventional technology known to those skilled in the art. The antibody can be purified and isolated using known techniques and bound to a support surface using known procedures. The resulting surface having antibody bound thereon can be used to assay a test sample, e.g., a biological sample, in vitro to determine if the sample contains one or more types of BCMA polypeptides. For example, antibodies which bind only to a specific BCMA epitope can be attached to the surface of a material. Alternatively, a plurality of specific antibodies, which may be arranged in an array, wherein antibodies specific for two or more different BCMA epitopes are attached to the solid support, can be used. A test sample is brought into contact with the antibodies bound to the surface of material. Specific binding can be detected using any known method. If specific binding is not detected, it can be deduced that the sample does not contain the specific BCMA epitope. As one non-limiting example of how specific binding can be detected, once the test sample has been contacted with the antibodies bound to the solid support, a second, detectably-labeled antibody can be added, which recognizes a BCMA epitope distinct from the epitope recognized by the solid support-bound antibody.

A variety of other reagents may be included in the assays to detect BCMA polypeptides described herein. These include reagents such as salts, neutral proteins, e.g. albumin, detergents, etc., that are used to facilitate optimal protein-protein binding, and/or reduce non-specific or background interactions. Reagents that improve the efficiency of the assay, such as protease inhibitors, anti-microbial agents, etc. may be used. The components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e. g. CD2 or CD3), or Fc receptors for IgG (FcyR), such as FcyRI (CD64), FcyRII (CD32) and FcyRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e. g. saporin, anti-interferon-, vinca alkaloid, ricin A chain, methotrexate or radioactive isotope hapten).

Bispecific antibodies can be prepared as full length antibodies or antibody fragments (e. g. F (ab') 2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305: 537-539 (1983)).

Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO93/08829, and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs-encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121: 210 (1986). According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e. g. tyrosine or tryptophan). Compensatory "cavities" of identical or similar size to the large side chain(s) are created on the interface of the second antibody molecule by replacing large amino acid side chains with smaller ones (e. g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al, Science, 229: 81 (1985) describe a procedure wherein intact antibodies are proteolytically cleaved to generate F (ab') 2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F (ab') 2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148 (5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al, Proc. Natl. Acad. Sci. USA, 90: 6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunology, 152: 5368 (1994). Antibodies with more than two valencies are also contemplated. For example, trispecific antibodies can be prepared. Tuttet al., J. Immunol. 147: 60(1991).

Diagnostic Assays

The invention further provides methods for detecting the presence of and/or a level of BCMA mRNA in a biological sample; and methods for detecting the presence of and/or a level of BCMA polypeptide in a biological sample.

In other embodiments, a method is provide for detecting a level of BCMA mRNA in a biological sample derived from an individual, comprising analyzing a polynucleotide sample from an individual for the level of BCMA polypeptide-encoding mRNA. The level of BCMA mRNA may be associated with autoimmune disease.

In still other embodiments, a method is provided for detecting the presence of and/or the level of a BCMA polypeptide in a biological sample.

A number of methods are available for determining the expression level of a BCMA nucleic acid molecule, e.g., a BCMA mRNA, or BCMA polypeptide in a particular sample. Diagnosis may be performed by a number of methods to determine the absence or presence or altered amounts of normal or abnormal BCMA mRNA in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. The presence and/or the level of a BCMA polypeptide may also be detected and/or quantitated in any way known to one of ordinary skill.

In addition, a test can include measurements of the expression of BCMA mRNA. Biochemical studies may be performed to determine whether a sequence polymorphism in a BCMA coding region or control regions is associated with disease. Disease associated polymorphisms may include deletion or truncation of the gene, mutations that alter expression level, that affect the activity of the protein, etc.

Changes in the promoter or enhancer sequence that may affect expression levels of BCMA can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Diagnostic methods of the subject invention in which the level of BCMA gene expression is of interest will typically involve comparison of the BCMA nucleic acid or protein abundance of a sample of interest with that of a control value to determine any relative differences, where the difference may be measured qualitatively and/or quantitatively, which differences are then related to the presence or absence of an abnormal BCMA gene expression pattern. A variety of different methods for determine the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

By a gene whose expression level is "correlated with" or "associated with" a particular physiologic state, it is intended a gene whose expression shows a statistically significant correlation with the physiologic state. The strength of the correlation between the expression level of a differentially expressed gene and the presence or absence of a particular physiologic state may be determined by a statistical test of significance. Methods for determining the strength of a correlation between the expression level of a differentially-expressed gene and a particular physiologic state by assigning a statistical score to the correlation are reviewed in Holloway et al. (2002) *Nature Genetics Suppl.* 32:481-89, Churchill (2002) *Nature Genetics Suppl.* 32:490-95, Quackenbush (2002) *Nature Genetics Suppl.* 32: 496-501; Slonim (2002) *Nature Genetics Suppl.* 32:502-08; and Chuaqui et al. (2002) *Nature Genetics Suppl.* 32:509-514; each of which is herein incorporated by reference in its entirety.

Additional tests that have been associated with autoimmune disease severity or progression can be combined with the BCMA test described above to render a full diagnosis or outlook result.

For example, the American College of Rheumatology has developed 11 criteria to diagnose SLE, which span the clinical spectrum of SLE in aspects of skin, systemic, and laboratory tests. These criteria include malar rash, discoid rash, sensitivity to sun light, oral ulcers, arthritis, serositis, kidney and central nervous system inflammation, blood alterations, and the presence of antinuclear antibodies. A patient must meet four of these criteria in order to be classified as a SLE patient. (Tan et al. (1982) Arthritis Rheumatol. 25:1271-1277). SLE is usually confirmed by tests including, but not limited to, blood tests to detect anti-nuclear antibodies; blood and urine tests to assess kidney function; complement tests to detect the presence of low levels of complement that are often associated with SLE; a sedimentation rate (ESR) or C-reactive protein (CRP) to measure inflammation levels; X-rays to assess lung damage and EKGs to assess heart damage.

Monitoring Effects of Drug Treatment

Monitoring the influence of agents (e.g., drugs, compounds) on the expression or BCMA protein (e.g., modulation of transcriptional activation) can be applied not only in basic drug screening, but also in clinical trials. For example, the effectiveness of an agent determined by a screening assay as described herein to decrease BCMA gene expression, or protein levels, can be monitored in clinical trials of subjects exhibiting decreased BCMA gene expression or protein levels. In such clinical trials, the expression or activity of a BCMA gene, and preferably, other genes that have been implicated in, for example, a disorder associated with levels of BCMA protein can be used as a "read out" or markers of the phenotype of a particular cell, in the present case, B cells.

In some embodiments, the present invention provides a method for monitoring the effectiveness of treatment of a subject with an agent (e.g., an agonist, antagonist, peptidomimetic, protein, peptide, nucleic acid, small molecule, or other drug) comprising the steps of (i) obtaining a pre-administration sample from a subject prior to administration of the agent; (ii) detecting the level of expression of a BCMA protein or mRNA, in the pre-administration sample; (iii) obtaining one or more post-administration samples from the subject, (iv) detecting the level of expression or activity of the BCMA protein or mRNA in the post-administration samples; (v) comparing the level of expression or activity of the BCMA protein or mRNA in the pre-administration sample with the BCMA protein or mRNA in the post administration sample or samples; and (vi) altering the administration of the agent to the subject accordingly. According to such an embodiment, BCMA expression or activity may be used as an indicator of the effectiveness of an agent, even in the absence of an observable phenotypic response.

The basal expression level of BCMA in different tissue may be determined by analysis of tissue samples from individuals typed for the presence or absence of a specific polymorphism. Any convenient method may be use, e.g. ELISA, RIA, etc. for protein quantitation, northern blot or other hybridization analysis, quantitative RT-PCR, etc. for mRNA quantitation. The tissue specific expression is correlated with the genotype.

The alteration of BCMA expression in response to a modifier is determined by administering or combining the candidate modifier with an expression system, e.g. animal, cell, in vitro transcription assay, etc. The effect of the modifier on BCMA transcription and/or steady state mRNA levels is determined. As with the basal expression levels, tissue specific interactions are of interest. Correlations are made between the ability of an expression modifier to affect BCMA levels, and the presence of the provided polymorphisms. A panel of different modifiers, cell types, etc. may be screened in order to determine the effect under a number of different conditions.

Treatment Methods

The present invention provides a method of treating an individual clinically diagnosed with a condition associated with increased BCMA levels on the B cell surface. The methods generally comprises analyzing a biological sample to measure BCMA levels and comparing such levels to those present in healthy controls. A treatment plan that is most effective for individuals clinically diagnosed as having a condition associated with increased BCMA levels, such as autoimmune disease, is then selected. Thus, the invention further provides a method for predicting a patient's likelihood to respond to a drug treatment for a condition associated with increased BCMA levels, comprising determining a patient's expression of a BCMA gene, wherein the presence of a increased BCMA levels associated with an autoimmune condition, such as SLE, and is predictive of the patient's likelihood to respond to a drug treatment for the condition.

Thus, another aspect of the invention provides methods for tailoring an individual's therapeutic treatment with BCMA expression according to that individual's drug response. Pharmacogenomics allows a clinician or physician to target prophylactic or therapeutic treatments to patients who will most benefit from the treatment and to avoid treatment of patients who will experience toxic drug-related side effects.

Autoimmune Diseases

The following is a non-limiting list of the possible autoimmune diseases that treatment thereof could be aided by the use of the BCMA measuring assay presently disclosed. B-cell regulated autoimmune diseases include arthritis (rheumatoid arthritis, juvenile rheumatoid arthritis, osteoarthritis, psoriatic arthritis), psoriasis, dermatitis including atopic dermatitis; chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), respiratory distress syndrome, adult respiratory distress syndrome (ARDS), meningitis, allergic rhinitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), lupus (including nephritis, non-renal, discoid, alopecia), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, antiphospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, etc), graft versus host disease (GVHD), pemphigoid bullous, pemphigus (all including vulgaris, foliaceus), autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, Lymphoid interstitial pneumonitis (HIV), bronchiolitis obliterans (non-transplant) vs NSIP, Guillain-Barre' Syndrome, Large Vessel Vasculitis (including Polymyalgia Rheumatica and Giant Cell (Takayasu's) Arteritis), Medium Vessel Vasculitis (including Kawasaki's Disease and Polyarteritis Nodosa), ankylosing spondylitis, Berger's Disease (IgA nephropathy), Rapidly Progressive Glomerulonephritis, Primary biliary cirrhosis, Celiac sprue (gluten enteropathy), Cryoglobulinemia, ALS, and coronary artery disease.

BLyS and/or APRIL Antagonists

If high levels of BCMA on a B cell surface of a patient suffering from an autoimmune disease are seen, this suggests the likelihood that the patient will respond favorably to inhibition of BLyS and/or APRIL. Thus, the present invention also comprises BLyS and/or APRIL antagonists that are used for the treatment of autoimmune diseases wherein the patient has elevated levels of BCMA protein expression on the surface of their B cells. The following are representative examples of BLyS and/or APRIL antagonists that could be utilized to treat such patients. For the purposes of functioning as a BLyS and/or APRIL antagonist, the extracellular domain of any of the TNFR family receptors is a polypeptide essentially free of the transmembrane or cytoplasmic domains that generally retains the ability to bind BLyS. Specifically, the extracellular domain of TACI can comprise amino acids 1 to 154 of the TACI polypeptide sequence (SEQ ID NO: 2). Additionally, the ECD can be fragments or variants of this sequence, such as ECD forms of TACI as described in von Bulow et al., supra, WO 98/39361, WO 00/40716, WO 01/85782, WO 01/87979, and WO 01/81417. In particular, these ECD forms can comprise amino acids 1-106 of SEQ ID NO:2, amino acids 1-142 of SEQ ID NO:2, amino acids 30-154 of SEQ ID NO:2, amino acids 30-106 of SEQ ID NO:2, amino acids 30-110 of SEQ ID NO:2, amino acids 30-119 of SEQ ID NO:2, amino acids 1-166 of SEQ ID NO:2, amino acids 1-165 of SEQ ID NO:2, amino acids 1-114 of SEQ ID NO: 2, amino acids 1-119 of SEQ ID NO:2, amino acids 1-120 of SEQ ID NO:2, and amino acids 1-126 of SEQ ID NO:2. In addition, the TACI ECD can comprise those molecules having only one cysteine rich domain.

ECD forms of BAFF-R include those comprising amino acids 1-71 of the BAFF-R polypeptide sequence (SEQ ID NO: 4). Additionally, the ECD can be fragments or variants of this sequence such as ECD forms of BAFF-R as described in WO 02/24909, WO 03/14294, and WO 02/38766. In particular, these ECD forms can comprise amino acids 1-77 of SEQ ID NO: 4, amino acids 7-77 of SEQ ID NO:4, amino acids 1-69 of SEQ ID NO:4, amino acids 7-69 of SEQ ID NO:4, amino acids 2-62 of SEQ ID NO:4, amino acids 2-71 of SEQ ID NO:4, amino acids 1-61 of SEQ ID NO:4 and amino acids 2-63 of SEQ ID NO:4, amino acids 1-45 of SEQ ID NO:4, amino acids 1-39 of SEQ ID NO:4, amino acids 7-39 of SEQ ID NO:4, amino acids 1-17 of SEQ ID NO:4, amino acids 39-64 of SEQ ID NO:4, amino acids 19-35 of SEQ ID NO:4, and amino acids 17-42 of SEQ ID NO:4. In addition, the BAFF-R ECD can comprise those molecules having a cysteine rich domain.

ECD forms of BCMA include those comprising amino acids 1-48 of the BCMA polypeptide sequence (SEQ ID NO: 6). Additionally, the ECD can be fragments or variants of this sequence, such as ECD forms of BCMA as described in WO 00/40716 and WO 05/075511. In particular, these ECD forms can comprise amino acids 1-150 of SEQ ID NO:6, amino acids 1-48 of SEQ ID NO:6, amino acids 1-41 of SEQ ID NO:6, amino acids 8-41 of SEQ ID NO:6, amino acids 8-37 of SEQ ID NO:6, amino acids 8-88 of SEQ ID NO:6, amino acids 41-88 of SEQ ID NO:6, amino acids 1-54 of SEQ ID NO:6, amino acids 4-55 of SEQ ID NO:6, amino acids 4-51 of SEQ ID NO:6, and amino acids 21-53 of SEQ ID NO:6. In addition, the BCMA ECD can comprise those molecules having only a partial cysteine rich domain.

In a further embodiment, the BLyS binding region of a BLyS receptor (e. g., an extracellular domain or fragment thereof of BAFF-R, BCMA or TACI) can be fused to an Fc portion of an immunoglobulin molecule to facilitate its solubility in vivo. According to one embodiment, the BLyS and/or APRIL antagonist binds to a BLyS polypeptide with a binding affinity of 100 nM or less. According to another embodiment, the BLyS and/or APRIL antagonist binds to a BLyS polypeptide with a binding affinity of 10 nM or less. According to yet another embodiment, the BLyS and/or APRIL antagonist binds to a BLyS polypeptide with a binding affinity of 1 nM or less.

In another example, BLyS and/or APRIL antagonists include BLyS binding polypeptides that are not native sequences or variants thereof. Some examples of such polypeptides are those having the sequence of Formula I, Formula II, Formula III as described in WO 05/000351. In particular, some binding polypeptides include ECFDLL-VRAWVPCSVLK (SEQ ID NO:13), ECFDLLVRHWVP-CGLLR (SEQ ID NO:14), ECFDLLVRRWVPCEMLG (SEQ ID NO:15), ECFDLLVRSWVPCHMLR (SEQ ID NO:16), ECFDLLVRHWVACGLLR (SEQ ID NO:17), or sequences listed in FIG. 32 of WO 05/000351.

Alternatively, the BLyS and/or APRIL antagonist can bind an extracellular domain of native sequence TACI, BAFF-R, or BCMA at its BLyS binding region to partially or fully block, inhibit or neutralize BLyS binding in vitro, in situ, or in vivo. For example, such indirect antagonist is a TACI antibody that binds in a region of TACI such that the binding of BLyS is sterically hindered. For example, binding at amino acids 72-109 or a neighboring region is believed to block BLyS binding. It could also be advantageous to block APRIL binding to this molecule, which is believed to occur in the region of amino acids 82-222. Another BLyS and/or APRIL antagonist is a BAFF-R antibody that binds in a region of BAFF-R such that binding of human BAFF-R to BLyS is sterically hindered. For example, binding at amino acids 23-38 or amino acids 17-42 or a neighboring region is believed to block BLyS binding. Finally, a further indirect antagonist would be a BCMA antibody that binds in a region of BCMA such that the binding of BLyS is sterically hindered. For example, binding at amino acids 5-43 or a neighboring region is believed to block BLyS (or APRIL) binding.

In some embodiments, a BLyS and/or APRIL antagonist according to this invention includes BLyS antibodies. The term "antibody" when referring to is used in the broadest sense and specifically covers, for example, monoclonal antibodies, polyclonal antibodies, antibodies with polyepitopic specificity, single chain antibodies, and fragments of antibodies. According to some embodiments, a polypeptide of this invention is fused into an antibody framework, for example, in the variable region or in a CDR such that the antibody can bind to and inhibit BLyS binding to TACI, BAFF-R, or BCMA or inhibits BLyS signaling. The antibodies comprising a polypeptide of this invention can be chimeric, humanized, or human. The antibodies comprising a polypeptide of this invention can be an antibody fragment. Alternatively, an antibody of this invention can be produced by immunizing an animal with a polypeptide of this invention. Thus, an antibody directed against a polypeptide of this invention is contemplated.

In particular, antibodies specific for BLyS that bind within a region of human BLyS (SEQ ID NO: 8) comprising residues 162-275 and/or a neighboring amino acid of amino acids selected from the group consisting of 162, 163, 206, 211, 231, 233, 264 and 265 of human BLyS are contemplated. The binding of the antibodies are such that the antibody sterically hinders BLyS binding to one or more of its receptors. Such antibodies are described in WO 02/02641 and WO 03/055979. A particularly preferred antibody is the one described as Lymphostat-B (Baker et al. (2003) Arthritis Rheum, 48, 3253-3265).

Other Immunosuppressive Drugs

The present method contemplates the use of other immunosuppressive drugs either singly or in combination with a BLyS, APRIL or BCMA inhibitor. These other drugs include, but are not limited to, immunosuppressive agents such as calcineurin inhibitors (e.g., cyclosporin A or FK506), steroids (e.g., methyl prednisone or prednisone), or immunosuppressive agents that arrest the growth of immune cells(e.g., rapamycin), anti-CD40 pathway inhibitors (e.g., anti-CD40 antibodies, anti-CD40 ligand antibodies and small molecule inhibitors of the CD40 pathway), transplant salvage pathway inhibitors (e.g., mycophenolate mofetil (MMF)), IL-2 receptor antagonists (e.g., Zeonpax© from Hoffmann-1a Roche Inc., and Simulet from Novartis, Inc.), or analogs thereof, cyclophosphamide, thalidomide, azathioprine, monoclonal antibodies (e.g., Daclizumab (anti-interleukin (IL)-2), Infliximab (anti-tumor necrosis factor), MEDI-205 (anti-CD2), abx-cb1 (anti-CD147)), and polyclonal antibodies (e.g., ATG (anti-thymocyte globulin)).

In one embodiment, a therapeutically effective amount of a BCMA antagonist (such as an antibody that binds the extracellular domain of BCMA) can be administered to a subject in combination with a therapeutically effective amount of rituximab. Such methods allow for the improved depletion and/or neutralization of B cells from said subject. Co-administration of such compounds can occur simultaneously or consecutively and through any effective route of administration.

As used herein, "a therapeutically effective amount" of an agent of interest is an amount which, when administered to a subject, is sufficient to achieve a desired effect, such as the depletion and/or neutralization of B-cells in a subject being treated with that composition.

In some embodiments a "therapeutically effective amount" or "effective amount" of a pharmaceutical composition containing a BCMA antagonist or an anti-CD 20 agent such as rituximab is from about 0.1 to about 200 mg/kg body weight in single or divided doses; for example from about 1 to about 100 mg/kg, from about 2 to about 50 mg/kg, from about 3 to about 25 mg/kg, or from about 5 to about 10 mg/kg. When animal assays are used, a dosage is administered to provide a target tissue concentration similar to that which has been shown to be effective in the animal assays. It is recognized that the method of treatment may comprise a single administration of a therapeutically effective amount or multiple administrations of a therapeutically effective amount of the BCMA antagonist (such as an antibody that binds the extracellular domain of BCMA) and the anti-CD 20 agent such as rituximab.

The term "anti-CD 20 agent" encompasses any molecule that binds to CD-20 and in the most preferred embodiment targets the cell associated with the CD-20 protein for killing. Such molecules include anti-CD-20 antibodies, such as RITUXAN® and follow-on versions of that agent such as ocrelizumab, a humanized version of that antibody, ofatumumbab (HuMax-CD20® a fully human anti-CD 20 agent), DXL625 (a second generation anti-CD20 monoclonal), GA101 (a third generation anti-CD20 agent that has an altered Fc region), the anti-CD20 molecules described in U.S. Application No. 20060121032, the anti-CD20 molecules described in U.S. Application No. 200700202059, the anti-CD20 molecules described in U.S. Application No. 20070014720, the anti-CD20 molecules described in U.S. Application No. 20060251652, the anti-CD20 molecules described in U.S. Application No. 20050069545, the anti-CD20 molecules described in U.S. Application No. 20040167319, TRU-015 (a small molecule immunopharmaceutical molecule that targets CD 20), as well as conjugated molecules such as ibritumomab (ZEVALIN®).

Pharmaceutical Formulations

Therapeutic formulations of the BLyS and/or APRIL antagonists such as BLyS-binding antibodies used in accordance with the present invention are prepared for storage by mixing an antibody having the desired degree of purity with optional pharmaceutically acceptable carriers, excipients or stabilizers (Remitgtorz's Phamamaceutical Science 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e. g. Zn-protein complexes);and/or non-ionic surfactants such as TWEEN, PLURONICS™ or polyethylene glycol (PEG)).

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e. g. one which acts on T cells, such as cyclosporin or an antibody that binds T cells, e. g. one which binds LFA-1). The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e. g. films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and .ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLE 1

Measurement of BCMA Levels on B Cells of Autoimmune Patients

Peripheral blood B cells were obtained by negative selection from 16 healthy controls (HC) and 15 SLE patients with whose disease activity was assessed by analysis of disease activity by SLEDAI. B cells were sub-grouped as CD19+ CD27− (naïve), CD19+CD27+ (memory) and CD19+ CD27high (plasmablasts). BAFF-R, TACI, and BCMA expression were compared by flow cytometry on each subset of B cells from SLE and healthy controls (HC) were compared by flow cytometry. The levels of serum BAFF-BLyS, APRIL and autoantibodies were quantified by ELISAs. In some experiments, BCMA-positive and -negative B cells were separated by flow cytometric sorting.

Figure 6A:
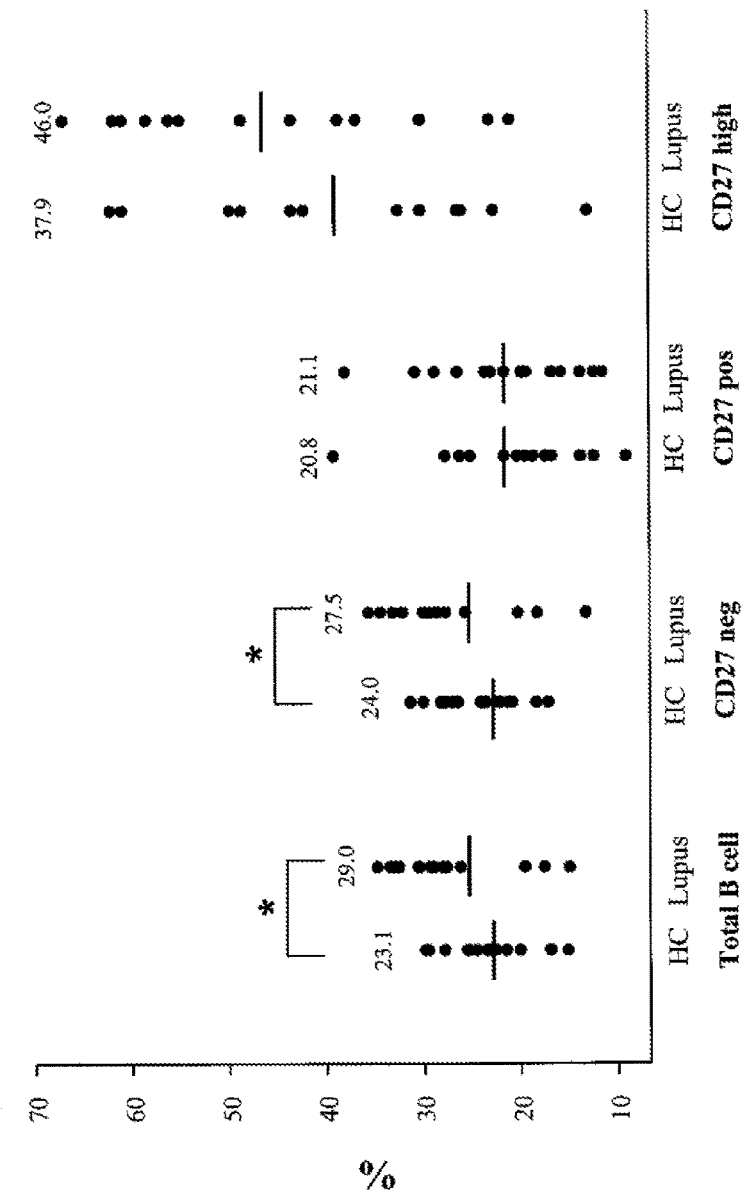
FIG. 6A graphs the percentage of BCMA positive cells comparing Healthy Controls (HC) and Lupus patients in naïve B cells (CD27 neg), memory cells (CD27 pos), and plasmablasts (CD27 high).
Figure 6B:
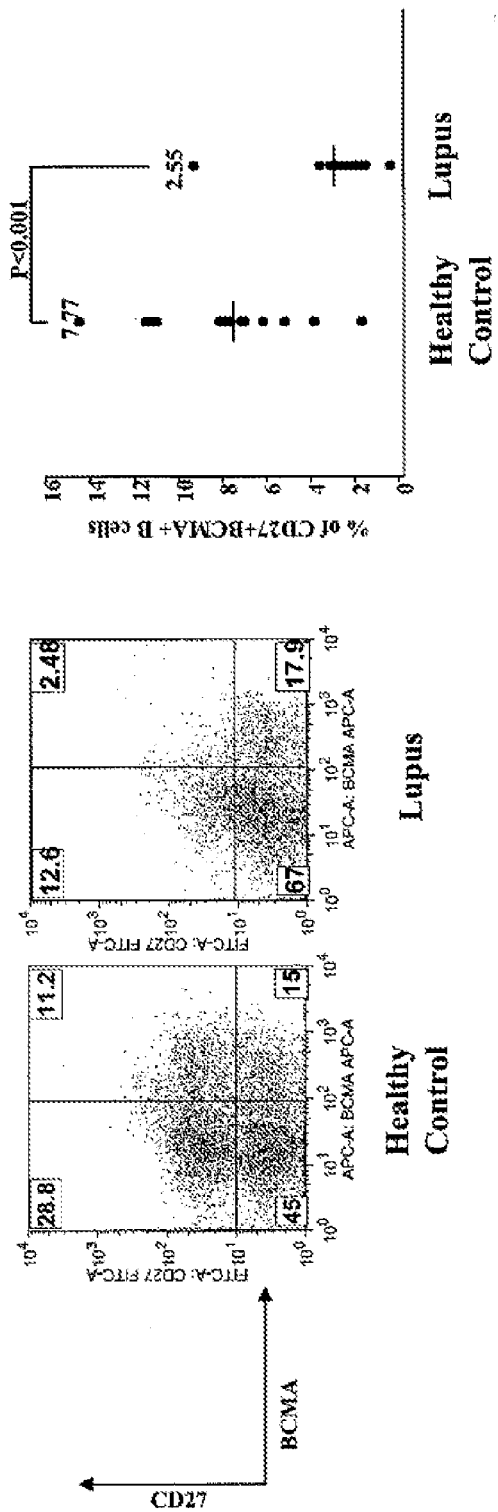
FIG. 6B graphs production of CD27 high (plasmablasts) vs the production of BCMA on the cell surface for Healthy controls and Lupus patients.
Figure 7:
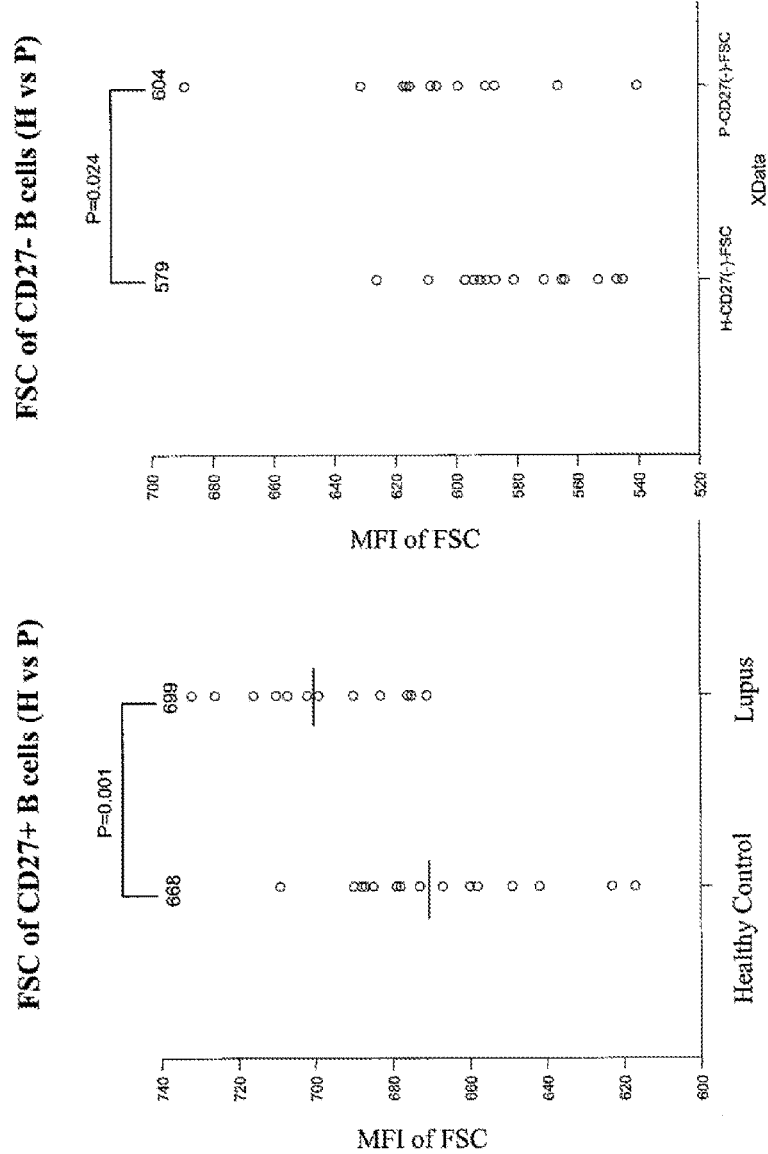
FIG. 7 reports the MFI of the FSC of CD27 pos and CD27 neg cells healthy controls vs. patients.
Figure 8A:
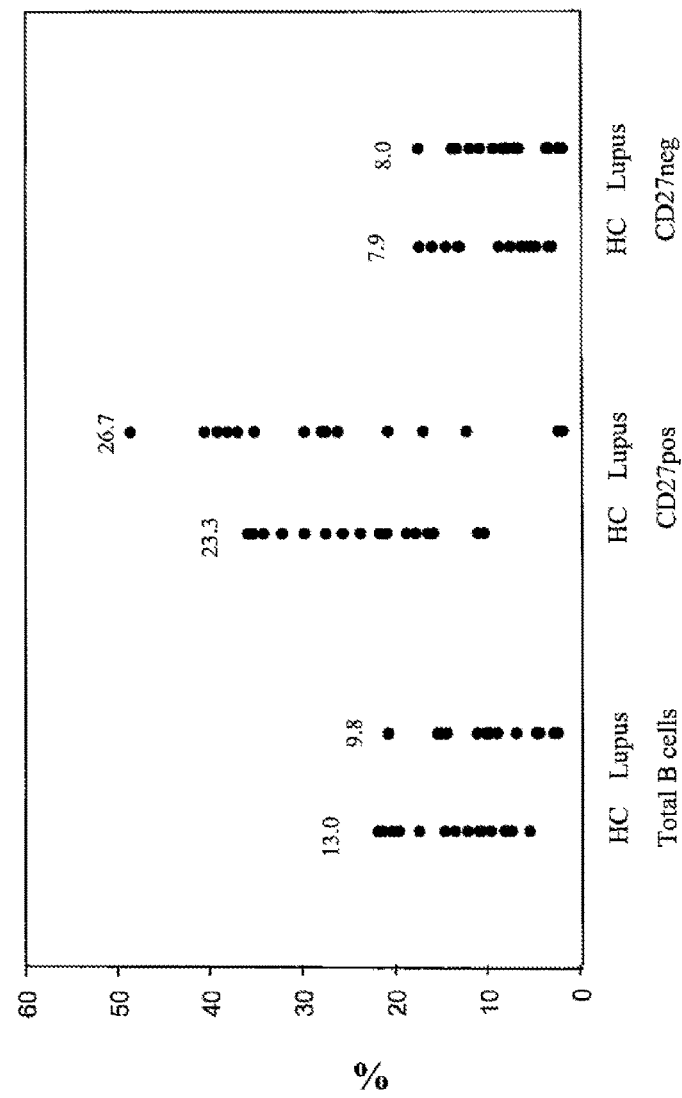
FIG. 8A discloses the percentage of CD19 high B cells found in Healthy Controls (HC) and Lupus patients in naïve B cells (CD27 neg), memory cells (CD27 pos), and plasmablasts (CD27 high).
Figure 8B:
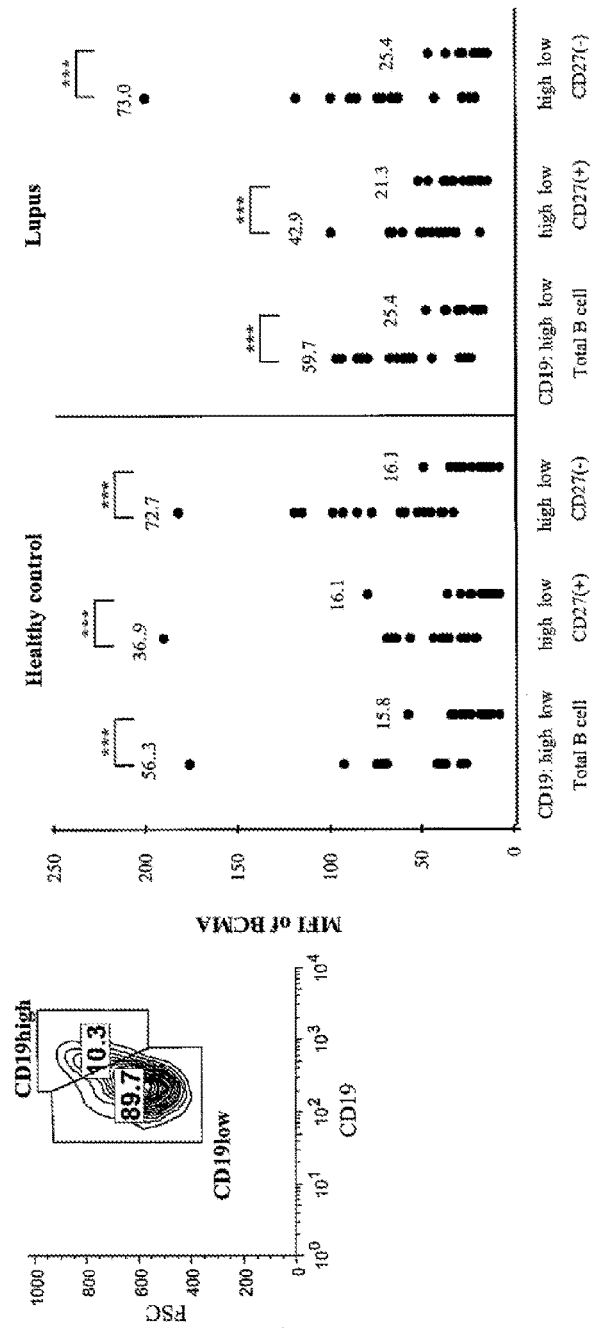
FIG. 8B charts the MFI of BCMA in CD19 high and CD19 low B cells for healthy controls and lupus patients.
Figure 9:
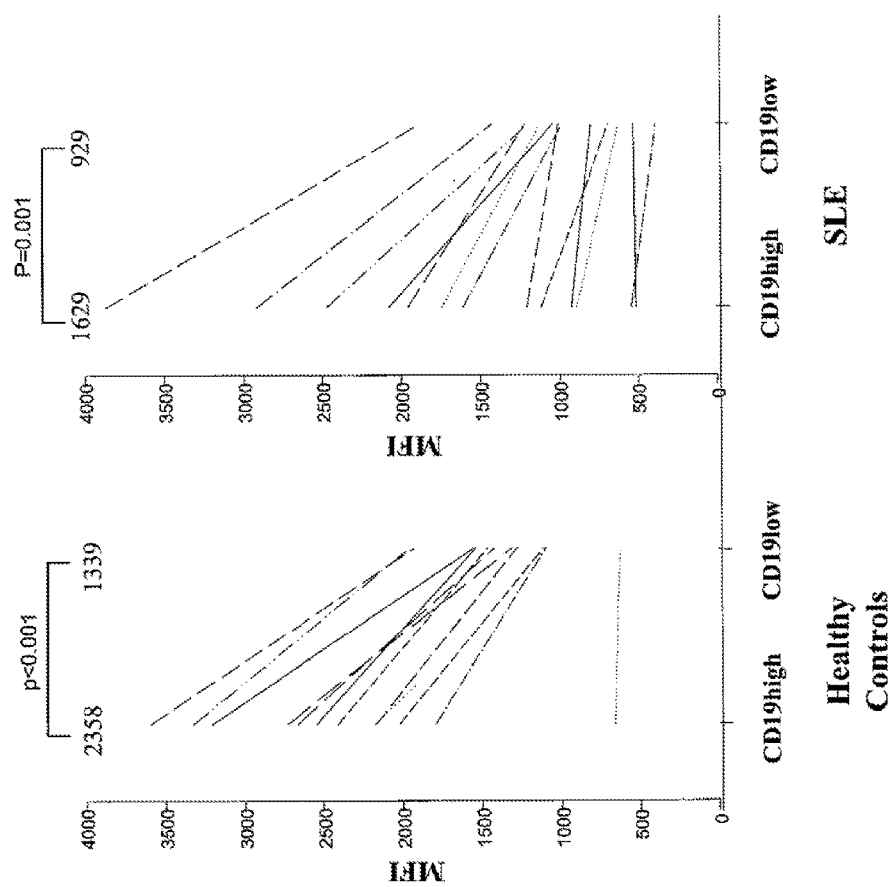
FIG. 9 graphically shows the levels of BAFF-R on the surface (by MFI) on the surface of CD19 high and CD19 low B cells for healthy controls and lupus patients.
Figure 10:
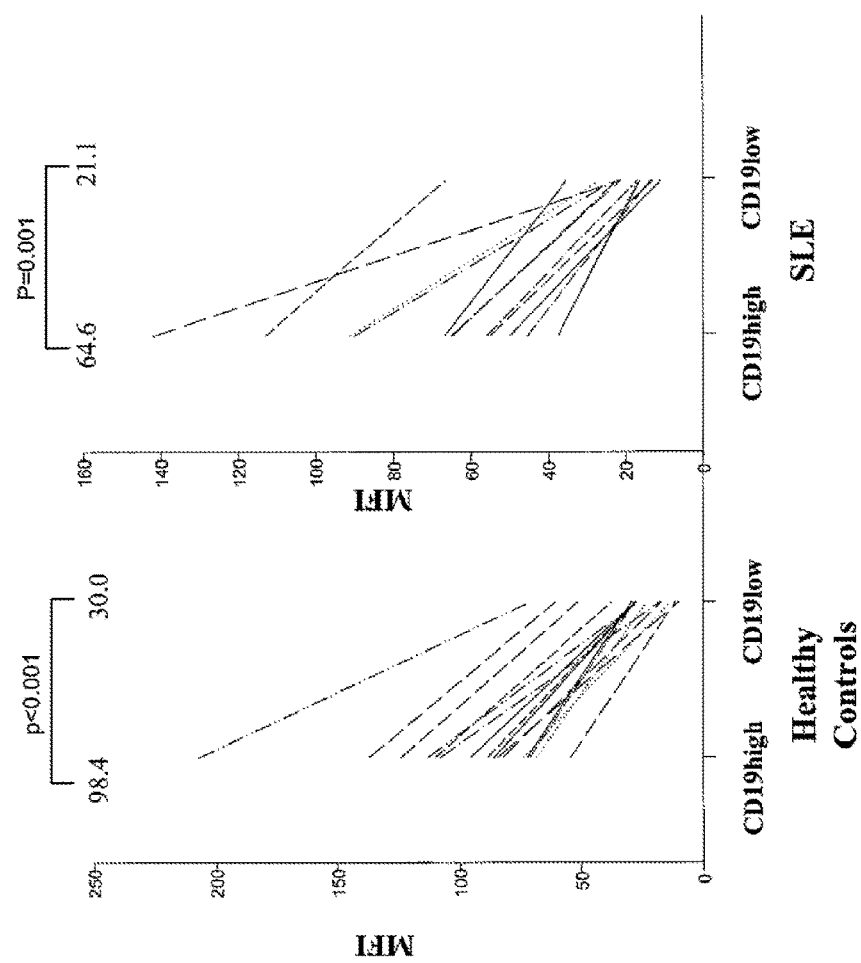
FIG. 10 graphically shows the levels of TACI on the surface (by MFI) on the surface of CD19 high and CD19 low B cells for healthy controls and lupus patients.

Expression Pattern of BAFF-R, TACI and BCMA in the Human Peripheral Blood B Cells Peripheral blood B cells were stained with anti-BAFF-R, anti-TACI and anti-BCMA antibodies. It has been shown that the expressions of BAFF receptors change with B cell maturation; hence, naïve (CD27−), memory B cells (CD27+) and plasmablasts (CD27high) were all analyzed separately. BAFF-R and TACI are detected in all the subsets but BAFF-R expression is low in plasmablasts and TACI expression is lower in naïve B cells (FIG. 1A). Even though it has been reported that BCMA expression is limited only in the plasma cells and germinal center B cells, we could also see the BCMA+ population in naïve and memory B cells from peripheral blood (FIG. 1A). This difference might be due to the different specificity of antibodies to the various transcript variants because BCMA was reported as having five transcript variants which are results of alternative splicing. Average of BCMA+ B cells are 24% in naïve B cells and 20.8% in memory B cells, which is lower than that of plasmablasts (37.9%) (FIG. 6A)

Expression of BAFF-R, TACI and BCMA on the B Cells in Controls and SLE Patients

Figure 1B:
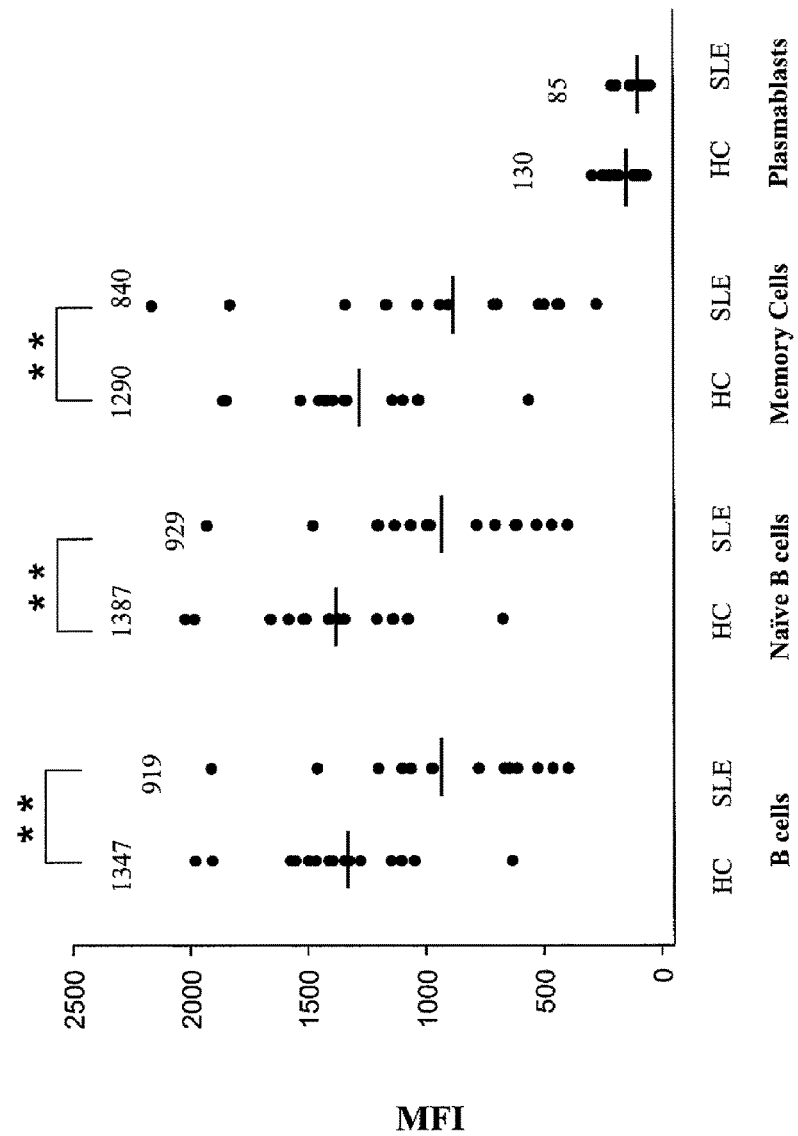
FIG. 1B graphs the median fluorescence intensity (MFI) of BAFF-R in total B cells, naïve B cells, memory cells, and plasmablasts comparing healthy controls (HC) and lupus patients (SLE).
Figure 1C:
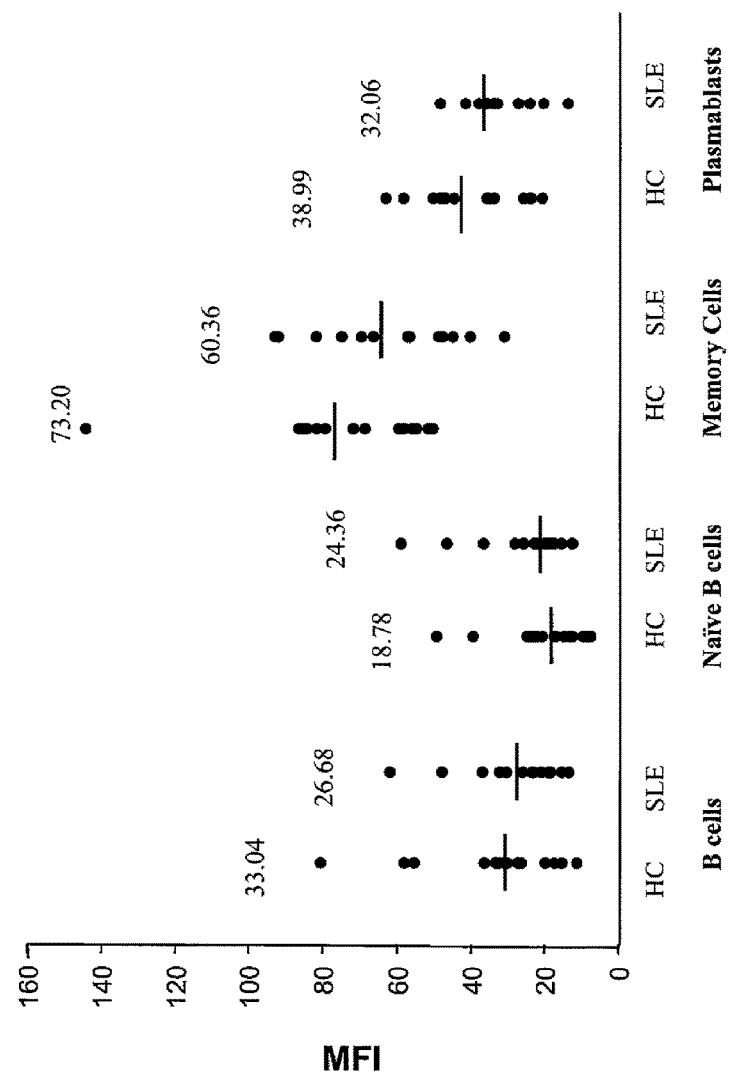
FIG. 1C graphs the median fluorescence intensity (MFI) of TACI in total B cells, naïve B cells, memory cells, and plasmablasts comparing healthy controls (HC) and lupus patients (SLE).

B cells from 15 patients with SLE and 16 non-autoimmune individuals were examined for expression of BAFF receptors. In the analysis of BAFF-R expression of the SLE and control groups, SLE patients showed significantly decreased BAFF-R expression in all three B cell subsets (MFI of control vs SLE, naïve=1387 vs 929, p=0.002; memory=1290 vs 840, p=0.003; plasmablasts=130 vs 85, p=0.077, FIG. 1B). TACI expressions of both two groups are not significantly different in all three subsets (MFI of control vs SLE, naïve=18.8 vs 24.4, p=0.144; memory=73.2 vs 60.4, p=0.121; plasmablasts=39.0 vs 32.1, p=0.110, FIG. 1C).

Figure 1D:
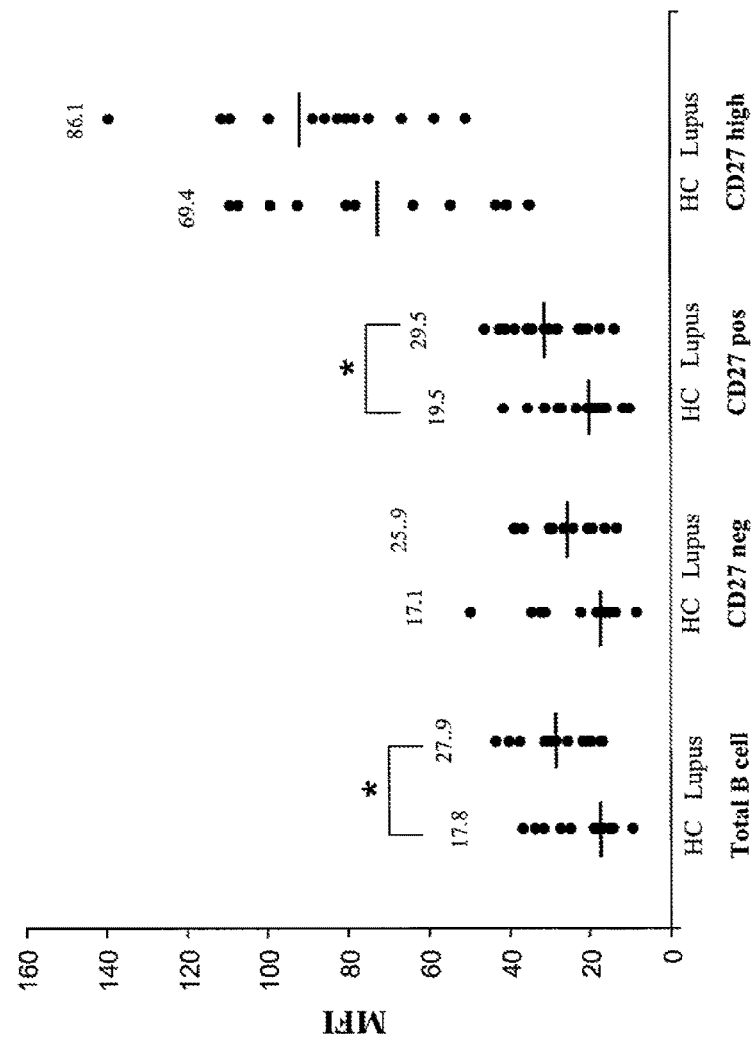
FIG. 1D graphs the median fluorescence intensity (MFI) of BCMA in total B cells, naïve B cells, memory cells, and plasmablasts comparing healthy controls (HC) and lupus patients (SLE).

The B cells from SLE had higher surface BCMA expression than normal controls (MFI of control vs SLE—17.8 vs 27.9, p=0.038; FIG. 1D). The BCMA expression of SLE in memory B cells is higher than that of normal controls (BCMA MFI of naïve B cells=19.5 vs 29.5, p=0.008, FIG. 1D). But the BCMA expression of naïve and plasmablasts are not significantly different.

Relationships of BAFF Receptors and Serum BAFF/APRIL Level, Auto-Antibodies, Disease Activity.

Figure 2:
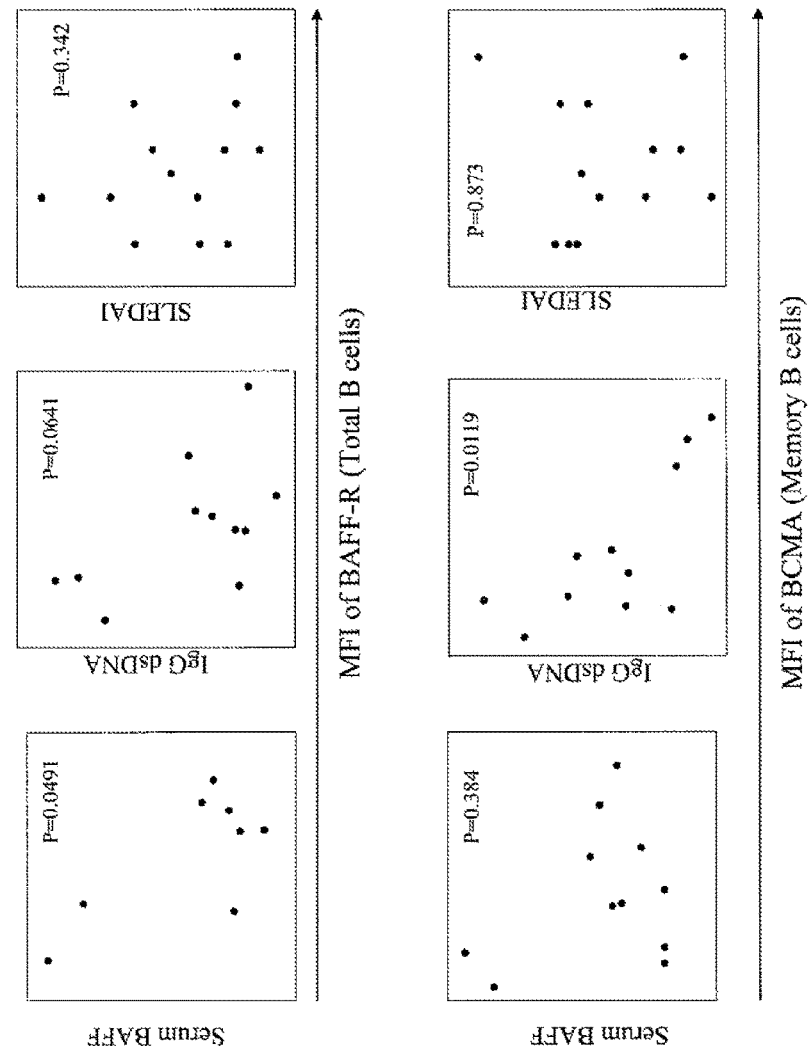
FIG. 2 upper level graphs the inverse relationship between BAFF-R expression on total B cells and serum BAFF (BCMA) but the lack of a statistically significant correlation between BAFF-R expression and serum IgG anti-dsDNA and SLEDAI score (disease activity).

There was an inverse correlation between BAFF-R expression of total B cells and serum BAFF (p=0.0491) but there was no significant correlation between BAFF-R expression and serum APRIL (FIG. 2). BAFF-R expression was inversely correlated with anti-dsDNA weakly (p=0.064) but not statistically significant. There was no correlation between BAFF-R and disease activity assessed by SLEDAI score (p=0.342, FIG. 2). MFI of BCMA positive memory cell is inversely correlated with serum IgG anti-dsDNA antibody levels (p=0.0119, FIG. 2) even though there's no significant correlation between BCMA and disease activity (SLEDAI) or serum BAFF level.

Characteristics of BCMA Positive B Cells

Figure 3A:
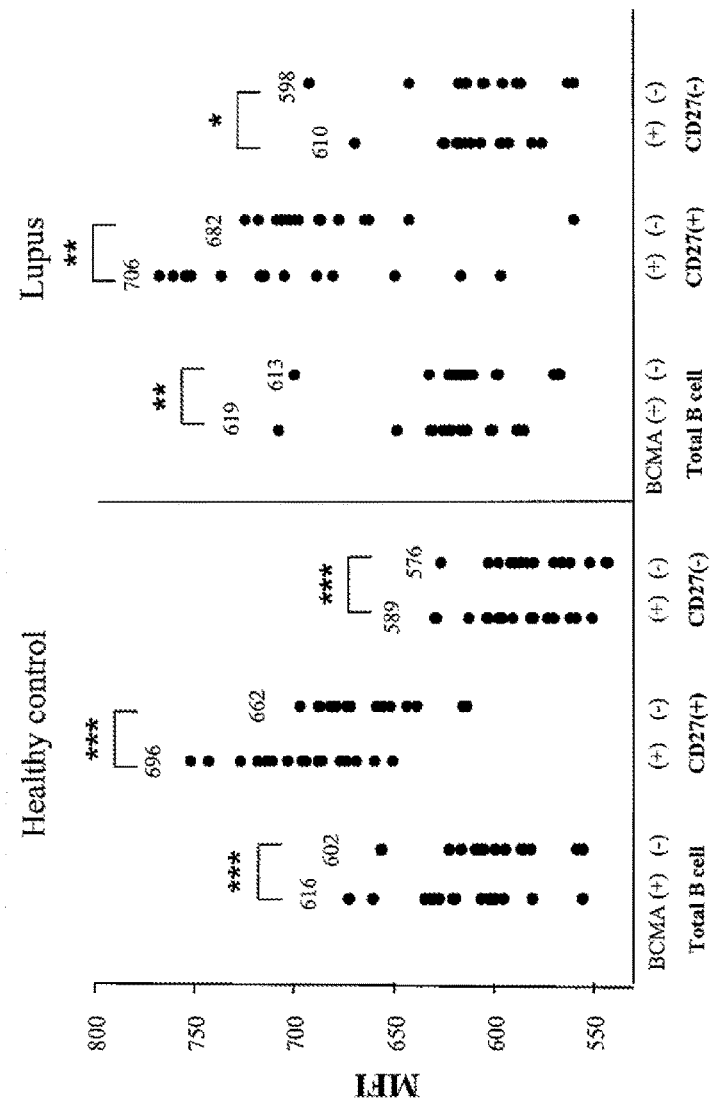
FIG. 3A graphs the forward angle light scatter (FSC) measured as MFI of the BCMA+ and BCMA− B cells in healthy controls and lupus patients. FSC is an indication of activation in B cells.

Lupus patients have increased BCMA expression on the naïve and memory B cells. We examined the characteristics of BCMA+ B cells to see the relations with autoimmunity. Mean FSC of BCMA+ and BCMA− cells in the each B cell subset was analyzed at first. Notably, lupus patients have the higher mean FSC than normal control indicating that the increased proportion of activated B cells in lupus as expected. BCMA+ B cells had higher mean FSC than BCMA− B cells in naïve B cells from both lupus and healthy controls (FIG. 3A). In memory B cells, BCMA+ B cells from healthy controls and lupus patients had significantly higher mean FSC than BCMA− B cells (FIG. 3A). These data might indicate that BCMA positive B cells in naïve and memory B cells are more activated B cells than BCMA negative B cells. This was true in both normal and SLE patients and there were no differences between them.

Figure 3B:
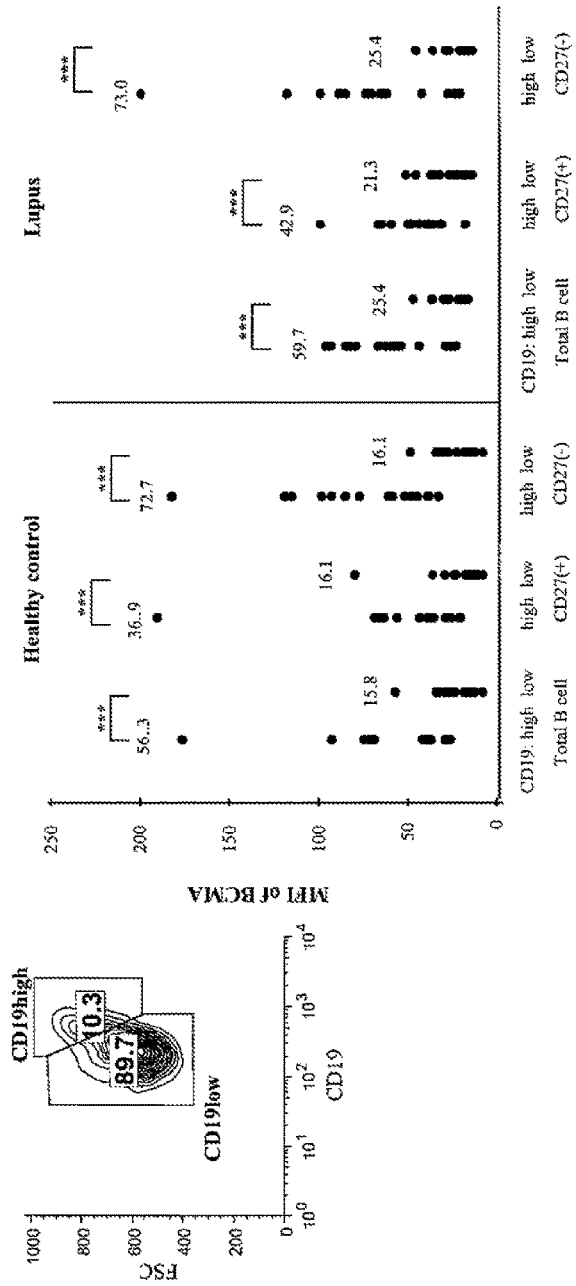
FIG. 3B shows the results of comparing CD19 high and CD 19 low B cells for the MFI of BCMA detection in both healthy controls and lupus patients.

We also analyzed BCMA expression on the CD19high population which was reported as increased in the lupus patients. We couldn't find significant differences between healthy controls and lupus patients in CD19high population in our study (Sup. FIG. 2) but CD19high B cells have much higher BCMA expressions than CD19low B cells in both healthy controls and lupus patients (FIG. 3B). Higher CD19 expression in BCMA+ B cells might be related with higher sensitivity to many immunologic responses including BCR signaling because CD19 is a BCR co-receptor that augments BCR signaling and partner of multiple receptors like CD21, CD40, CD38, CD72, VLA-4 and FcγRIIB.

Figure 4A:
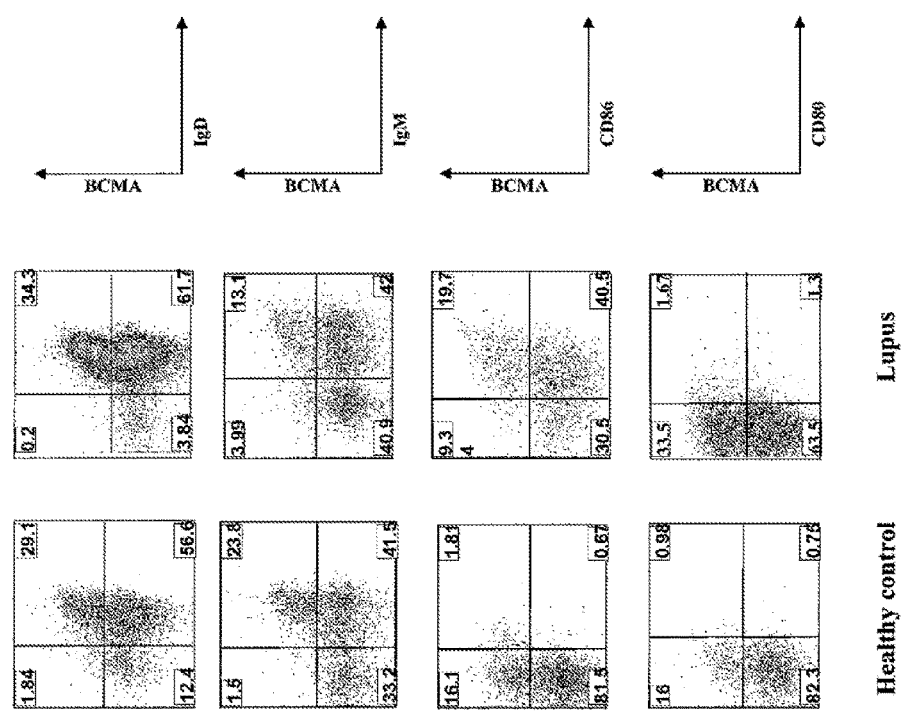
FIG. 4A shows results that indicate that BCMA+ cells are IgD+ and IgM+ and therefore have not undergone class switching. It also graphs the higher levels of CD86 seen in BCMA+ cells of lupus patients and the relatively low levels of CD80 seen in both healthy controls and lupus patients.
Figure 4B:
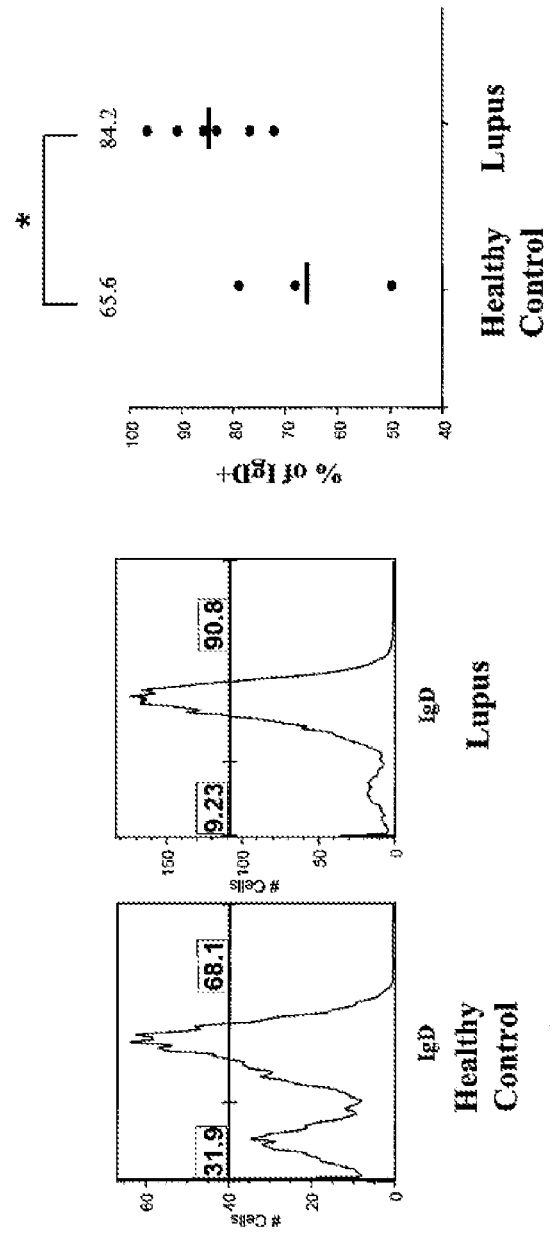
FIG. 4B graphs the higher percentage of IgD+ B cells seen in lupus patients as compared to healthy controls.

Most of the BCMA+ B cells are IgD+ and IgM+ in both lupus and healthy people, which means BCMA+ B cells are not class switched (FIG. 4A). Therefore, CD27− BCMA+ B cells might be included into the naïve B cell population. CD27+BCMA+ B cells also shows IgD+ and these cells could be un-class-switched memory B cells. Furthermore, lupus patients have higher percentage of IgD+ B cells than healthy control (FIG. 4B).

B cells of lupus patients are usually more activated than healthy people and it was reported that CD86 expression is much higher in lupus B cells. CD80 and CD86 expression of BCMA+ B cells were examined in lupus and healthy people. Lupus patients have much higher CD86 expressions and the percentage of CD86+ cells on the BCMA+ cells are higher than BCMA− cells. Healthy controls have lower CD86 expressions but percentage of CD86+ cells on the BCMA+ cells are higher than BCMA− cells. CD80 expressions were not high in both lupus and healthy controls (FIG. 4A). BAFF and APRIL plus CPG increased BCMA expression on all the subsets of B cells and induced expansion of plasmablasts and naïve B cells.

Figure 5A:
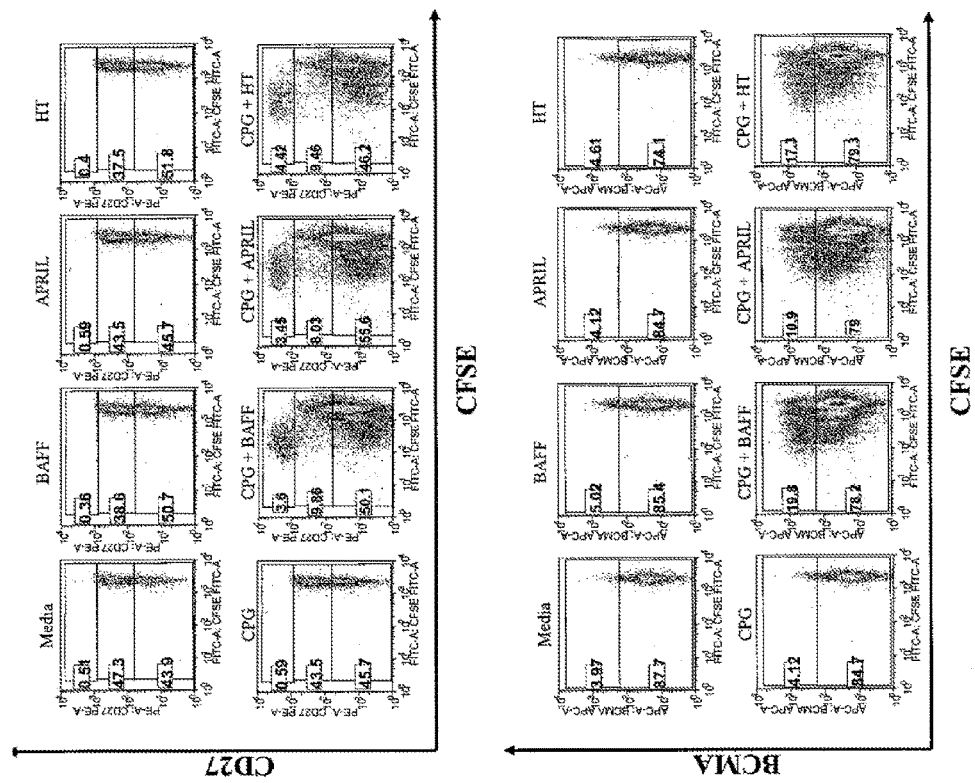
FIG. 5A discloses the results of labeling the peripheral blood mononuclear cells (PBMC) of healthy controls and lupus patients with 5-carboxyfluorescein diacetate succinimidyl ester (CSFE) and incubating with CpG with and without ligands. The upper level shows plasmablast induction (CD27 high) and the lower level shows BCMA induction.
Figure 5B:
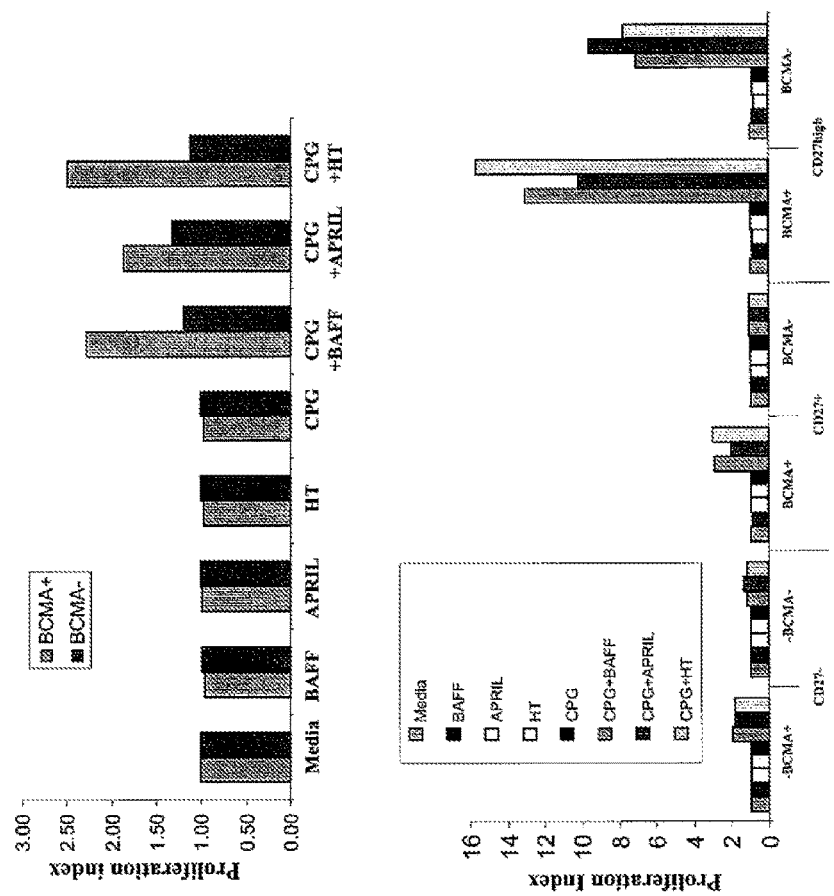
FIG. 5B graphs the experiment disclosed in 5A but focusing on the proliferation results.
Figure 5C:
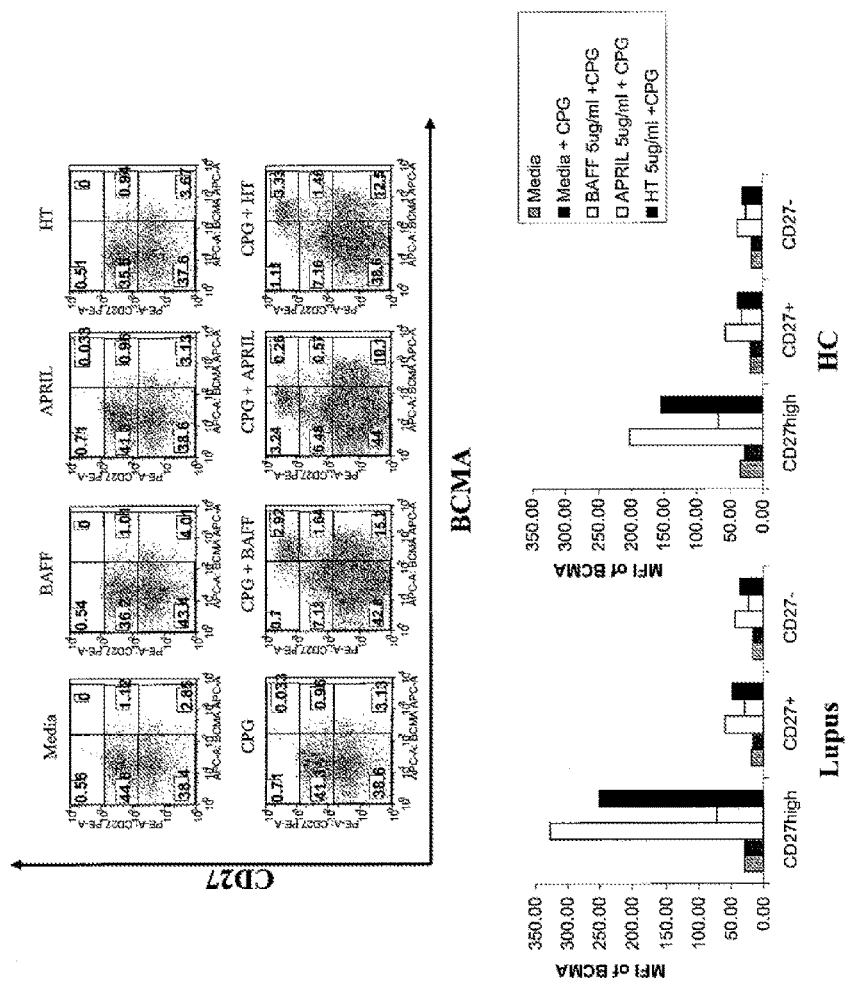
FIG. 5C upper level graphs the results from the experiment of 5A charting the increase of CD27 high cells with the increase of BCMA. The lower level reports the MFI of BCMA in this experiment in lupus and healthy controls with the various inductions.
Figure 5D:
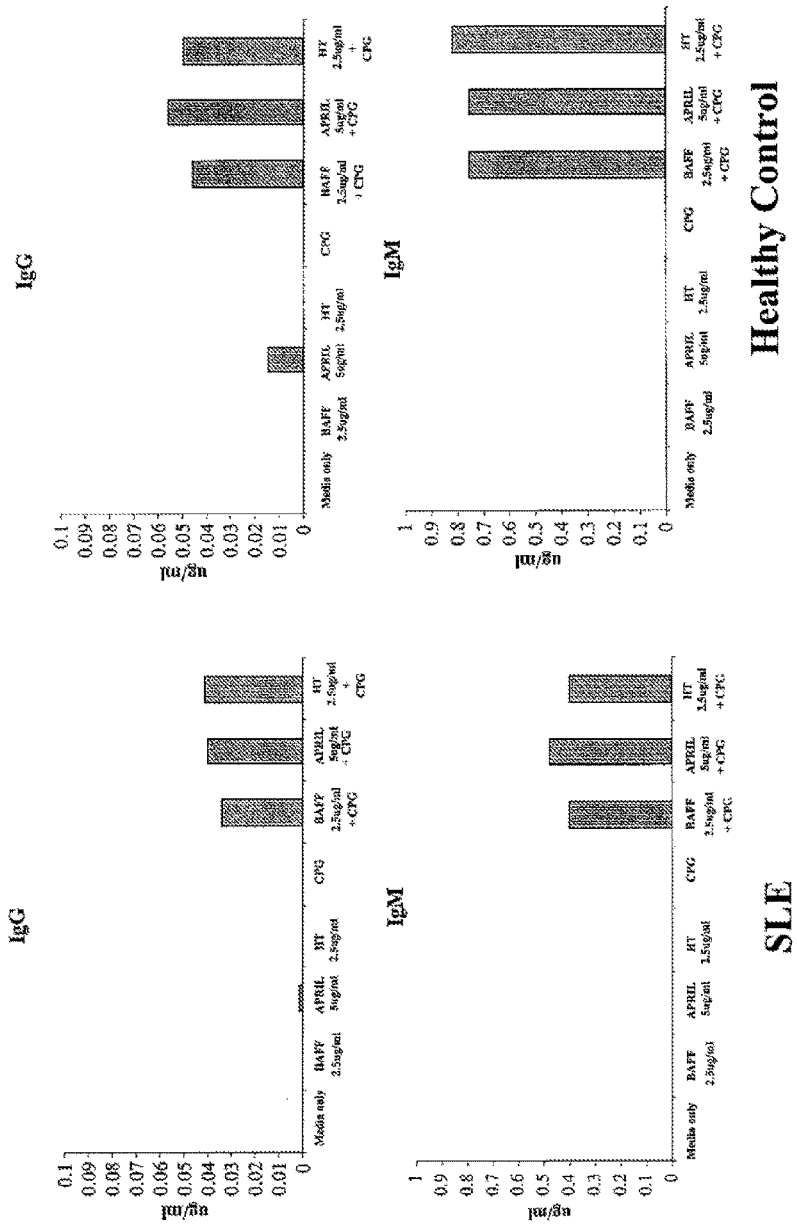
FIG. 5D discloses the production of IgG and IgM in the sorted B cells of the experiment disclosed in 5A.

B cells isolated from PBMC of lupus patient and healthy control were labeled with CFSE (Caroxy-fluorescein diacetate) and incubated with CPG (oligodeoxynucleotides containing a CpG motif) with or without BAFF, APRIL or HT. After 4 day incubation, BCMA expression on each subset of B cells and their proliferation were analyzed (FIG. 5A and FIG. 5C). CPG alone didn't increase BCMA expression. BCMA expressions on all the subsets of B cells were increased significantly by CPG+BAFF and CPG+HT, especially on CD27high plasmablasts. CPG+APRIL also increased BCMA expression slightly. BAFF, APRIL, and HT induced strong proliferation of CD27 high B cells and moderate proliferation of CD27− B cells (FIG. 5B). But CD27+ population was not expanded. Decrease of CD27+ memory B population could be due to CD27+ cells were differentiated to CD27high plasma cells or due to the lack of proliferation CD27+ B cells.

Ig Secretion and Auto-Antibody Production by BCMA+ and BCMA− B Cells

B cells are isolated from PBMC of lupus and healthy people by magnetic sorting (B cell enrichment kit. Stemcell, British Columbia, Canada). BCMA+ B cells are sorted from isolated B cells by FACS sorting. The sorted BCMA+ B cells are incubated with or without anti-CD40/IL4, anti-CD40/IL4/CPG, anti-CD40/IL4/BCR for 5 days in the 96-well culture plate. The IgM and IgG concentration and anti-dsDNA activity of supernatants were analyzed by ELISA.

Summary of Results:

Whereas BAFF-R expression on SLE B cells was significantly lower compared to its levels on HC B cells (MFI of control vs SLE, naïve=1387 vs 929, p=0.002; memory=1290 vs 840, p=0.003), BCMA expression was substantially higher on SLE B cells (MFI of control vs SLE: 18 vs 28, p=0.038). This was most pronounced in the memory B cell subset (MFI of control vs SLE=19 vs 29, p=0.008). BCMA levels were not correlated with either disease severity (SLEDAI) or with serum BLyS or APRIL levels. BCMA+ cells also tended to be larger than BCMA-negative cells, and had higher CD19 and CD86 expression, indicating a greater degree of activation. To examine the functional implications of differential BCMA expression, purified BCMA-positive or BCMA-negative B cells were incubated with BLyS, APRIL or BLyS/APRIL heterotrimers (HT) with or without the TLR9 stimulator, CpG. Whereas none of the ligands induced proliferation of the BCMA+ B cells on their own, the combination of CpG with each individual ligand induced substantial BCMA+ B cell proliferation.

Conclusions:

BCMA expression on B cells from patients with SLE is significantly increased, especially on memory B cells. BCMA positive cells have a more activated phenotype and produce higher amounts of immunoglobulin and autoantibodies. All 3 ligands, BLyS, APRIL or HT potently activate BCMA positive cells in the presence of CpG. These findings may help to explain the observed expansion of DNA reactive SLE B cells in the presence of BLyS and APRIL.

EXAMPLE 2

Combination Treatment with BCMA Antibodies and Rituximab in Human CD20 Transgenic Mice for the Depletion and/or Neutralization of B Cells BCMA expression is important for the survival of plasma cells. Gene targeting has confirmed that survival of long lived bone marrow derived from plasma cells was reduced in BCMA deficient mice. Since CD20 is not expressed on long lived plasma cells in the bone marrow, targeting these cells with blocking or cytotoxic antibodies to BCMA should deplete these cells which may contribute a significant component of the anti-CD20 resistant autoantibody producing cells in patients with SLE. Combining such treatment with rituximab will provide further beneficial results.

Rituximab does not bind to mouse CD20 and therefore cannot be used to deplete B cells in normal mice. Also, there are no commercially available anti-mouse CD20 mAbs effective for in vivo B cell depletion. Gong et al. (*J. Immunol* 174:817-826; 2005) utilized a strain of human CD20 transgenic mice (generated using bacterial artificial chromosome/BAC technology) that they could treat with anti-human CD20 mAbs (rituximab and ocrelizumab) and induce B cell depletion or neutralization similar to that observed in humans treated with these mAbs. This example utilizes a strain of hCD20 Tg mice disclosed in Ahuja et al., *J. Immunol* 179:3351-3361; 2007.

General approach: Use optimal doses of each therapeutic (BCMA antibody antagonists which binds to the extracellar domain of BCMA and rituximab), either sequentially or in combination and evaluate B cell depletion and/or neutralization. Assess B cell depletion at an optimal timepoint (3 weeks), but include additional groups to evaluate B cell recovery following treatment cessation (~20 weeks).

Materials and Methods

TABLE 1

| Treatment | Concentration | Final dose solution (mg/mL) | Volume/ mouse (mL) | Route | Schedule |
|---|---|---|---|---|---|
| PBS | — | — | 0.2 | SC | M/W/F x 3 weeks |
| BCMA antibody | Therapeutically effective dose | | | SC | M/W/F x 3 weeks (9 doses/mouse) |
| Rituxan (Rituximab) 10 mg/kg | stock = 10 mg/mL | 10.0 | 0.2-0.25 | IP | once a week for 2 or 3 weeks (three weekly doses for Groups 3 and 4; two weekly doses for Group 5) |

Animal Care, Acclimation, and Housing

Room temperature is maintained at 70-74° F. and humidity maintained at 30%-70%. A light/dark cycle of 12 hours is used, except when room lights may be turned on during the dark cycle to accommodate study-related activities. Each animal is offered rodent chow (irradiated 5056, Pico Lab, Richmond, Ind.) and water ad libitum. Procedures in this study are designed to avoid or minimize discomfort, distress, or pain to animals. Treatment of study animals is in accordance with conditions specified in the Guide for the Care and Use of Laboratory Animals (ILAR publication, 1996, National Academy Press). The animals are randomly assigned to the various treatment groups.

Treatment Groups: The period of dosing is designated as the dosing phase. The first day of dosing is designated "Day 1." The day prior to Day 1 is "Day −1." The day following the dosing phase terminal sacrifice is the first day of the recovery phase.

TABLE 2

| Group | 1st Treatment (route) | 2nd Treatment (route) | Dose schedule | Sac Day 23 | Sac Week ~20 |
|---|---|---|---|---|---|
| 1 | PBS (SC) | PBS (SC) | 3 times weekly | 5 | 6 |
| 2 | BCMA antibody Therapeutically effective dose (SC) | — | 3 times weekly for 3 weeks (total of 9 doses) | 5 | 5 |
| 3 | Rituximab 10 mg/kg (IP) | — | once weekly for 3 weeks (total of 3 doses) | 5 | 5 |
| 4 | Rituximab 10 mg/kg (IP) | BCMA antibody (SC) Therapeutically effective dose | Stagger treatments by 2 days; continue both treatments for 3 wks | 5 | 6 |
| 5 | BCMA antibody (SC) Therapeutically effective dose | Rituximab 10 mg/kg (IP) | BCMA antibody for 3 weeks (9 doses), Rituximab for last 2 weeks of BCMA antibody dosing period (2 doses) | 5 | 6 |

Rituximab is administered intraperitoneally (IP). The BCMA antibody and vehicle (PBS) is administered via subcutaneous (SC) injection within the subscapular region three times weekly (9 total doses). The first dose is administered on Day 1 (D1). In combination treatment groups, and where relevant, all animals receive the IP injection first, followed by administration of the SC injection within a period of 60 minutes. GROUP 4: rituximab 1st, then BCMA antibody; GROUP 5: BCMA antibody $1^{st}$, then rituximab. Dose volumes are adjusted weekly according to individual animal body weights.

Summary of Study Endpoints:

Whole blood (150 μL; EDTA) is collected and flow cytometry analysis performed for T and B cell subsets.

Serum (~100 μL whole blood placed in serum separator tubes) is collected at various timepoints for later analysis of total $IgG_1$, $IgG_{2a}$, IgM, IgE and IgA by Luminex assay.

At sac, spleens are collected and processed for flow analysis and later IHC/histology. Splenectomy is performed under isoflurane anesthesia prior to blood collection. Whole spleen is weighed and recorded before sectioning.

At sac, major peripheral lymph nodes (inguinal, axillary, brachial, cervical, and mesenteric) are collected for possible future IHC and histology. The lymph nodes are fixed with formalin or Zinc Tris buffer and stored in 70% alcohol for possible future use.

For histology: ⅓ spleen and 1 LLN (left LN) are placed into ZnTris and the same tissues (right LN) is collected into 10% NBF.

All animals in Groups 1-5 have serum (100 μL blood in serum separator tubes) and whole blood (150 μL in EDTA tubes) collected on day −5 via retro-orbital vein. Serum Collection: A minimum of 100 μL of whole blood is placed into serum separator tubes and allowed to clot for a minimum of 15 minutes. Blood is then spun at 4000 rpm for 10 minutes. A minimum of 50 μL of serum is aliquoted into a second container. Aliquots of serum are stored at ≤60° C.

Whole Blood in EDTA Collection: A minimum of 150 μL of blood is placed into a microtainer tube containing EDTA. The tubes are gently inverted a minimum of 20 times. Whole blood in EDTA samples are stored at room temperature until processed for flow cytometry.

All animals that are sacrificed are anesthetized with isoflurane. All sacrificed animals have blood, serum, spleen and major peripheral lymph nodes collected. The spleen is collected under isoflurane anesthesia prior to the blood sample to avoid altering splenocyte subsets. The whole spleen is weighed. The spleen is cut into 3 sections (cranial, middle & caudal), to be processed as shown in Table 3.

TABLE 3

Collection of Spleen Samples

| Spleen section[1] | Media | Use | Storage |
|---|---|---|---|
| Cranial | Zinc-Tris Buffer | IHC | Room Temperature |
| Middle | RPMI + 10% FBS | Flow Cytometry | 4 degrees Celsius |
| Caudal | 10% NBF | Histology | Room Temperature |

Lymph Node Collection: Major peripheral lymph nodes (inguinal, axillary, brachial, cervical and mesenteric) are collected for histology/IHC in cassettes.
   a. Cassettes containing Left Lymph Nodes (excluding mesenteric LN) for IHC are placed into Zinc Tris buffer.
   b. Cassettes containing Right Lymph Nodes (excluding mesenteric LN) for histology are placed into 10% NBF.
   c. Cassettes containing Mesenteric Lymph Nodes are collected into 10% NBF by taking the entire intestinal tract (from stomach to just above the rectum) whole and unflushed.

All samples are stored at room temperature.

TABLE 4

Collection of Lymph Nodes

| LN[1] | Media | Potential Use | Storage |
|---|---|---|---|
| Left LNs | Zinc-Tris Buffer | IHC | Room Temperature |
| Mesenteric | 10% NBF | Histology | Room Temperature |
| Right LNs | 10% NBF | Histology | Room Temperature |

Whole Blood Immunophenotyping: Briefly, whole blood is collected into BD Microtainer™ tubes containing $K_2$EDTA anticoagulant. A 50 μL aliquot of whole blood is incubated with the appropriate working antibody cocktail (see Table 5) and red blood cells are lysed. Prior to sample acquisition on the flow cytometer, Flow Count™ fluorescent microspheres are added to each sample tube for calculating absolute cell concentrations. Data acquisition is conducted on a BD FACSCalibur flow cytometer equipped with a 15 mW air-cooled Argon ion laser with 488 nm emission and a red-diode laser with 635 nm emission.

TABLE 5

Whole blood four-color monoclonal antibody panel

| Antibody Panel | Cell Type Identified | |
|---|---|---|
| CD45/B220/IgD/IgM | Total lymphocytes | [CD45+] |
| | Total B lymphocyte | [CD45+/B220+] |
| | Mature B lymphocytes | [CD45+/B220+/IgD+/IgM−] |
| | Immature B lymphocytes | [CD45+/B220+/IgD−/IgM+] |
| | Mature Naïve B lymphocytes | [CD45+/B220+/IgD+/IgM+] |
| CD3/B220/CD19/hu CD20 | Total T lymphocytes | [CD3+] |
| | Total B lymphocyte | [CD3−/B220+] |
| | B lymphocytes[1] | [B220+/CD19+/huCD20−] |
| | B lymphocytes[2] | [B220+/CD19+/huCD20+] |

[1]The phenotype [B220+/CD19+/huCD20−] describes a population of B cells expressing both B220 and murine CD19 surface antigen but not the human CD20 transgene.

[2]The phenotype [B220+/CD19+/huCD20+] describes a population of B cells expressing both B220 and murine CD19 surface antigen including the human CD20 transgene.

Spleen Immunophenotyping: Briefly, single cells are isolated and incubated with the appropriate antibody cocktails (see Table 6). Instrument calibration and data acquisition is conducted as for whole blood immunophenotyping.

TABLE 6

Spleen four-color monoclonal antibody panel

| ANTIBODY PANEL | B CELL SUBSET IDENTIFIED | |
|---|---|---|
| IgD/IgM/B220/ hCD20 | F(I) Mature | [B220+/IgM$^{low}$/IgD+] |
| | F(II) Less Mature | [B220+/IgM+/IgD+] |
| | F(III) Less Mature | [B220+/IgM+/IgD$^{low}$] |
| CD23/CD21/B220/ CD45 | MZ (marginal zone) | [B220+/CD21+/CD23$^{low}$] |
| | FO (follicular) | [B220+/CD21$^{low}$/CD23+] |
| | NF Newly Formed | [B220+/CD21−/CD23−] |
| IgM/CD21/B220/ CD45 | M (Mature) | [B220+/IgM$^{low}$/CD21$^{low}$] |
| | T2 (Transitional 2)/ MZ | [B220+/IgM+/CD21+] |
| | T1 (Transitional 1) | [B220+/IgM+/CD21−] |

IHC Analysis

Tissues: Test tissues includes samples from both spleens and lymph nodes. For the spleen samples, transverse sections of spleen (cranial and caudal pieces) from each animal is included. The cranial spleen sections (Zinc Tris-fixed) are stained with rat monoclonal antibody to CD45R/B220, CD138, or CD5 alone. A subset of tissue sections will also be stained with rat isotype IgG as a negative control. The caudal spleen sections (formalin-fixed) is stained with biotinylated PNA (if necessary to visualize GC; H&E may suffice) and H&E. A subset of tissue sections is also stained with biotinylated parathyroid hormone-related protein (PTHrP) as a negative control.

The lymph nodes examined from each animal include the inguinal, axillary, brachial, cervical, and mesenteric. The lymph nodes are fixed with formalin or zinc Tris and held in 70% alcohol for possible future use.

Antibodies: The antibodies used included three rat monoclonal antibodies to mouse CD45R/B220 (clone RA3-6B2, isotype: rat IgG2a, k; 0.5 mg/mL, #557390, BD Biosciences, San Jose, Calif.), CD5 (Ly-1, clone 53-7.3, 0.5 mg/mL, #553017, BD Biosciences), and CD138 (clone Syndecan-1, 0.5 mg/mL, #553712, BD Biosciences).

Statistical Analyses: Statistical analyses of group differences in organ weights, B cell counts, and immunoglobulin levels were conducted using analysis of variance (ANOVA).

Collection of the data outlined above will allow the percent change in absolute concentration of B cells in the mouse peripheral blood samples at various time points for the stated treatment group to be determined. Alternatively, the data can be expressed as a change in the percent of positive lymphocytes or B220+ cells. Such data will demonstrate that that the combination of anti-CD 20 agents and BCMA antagonists, such as RITUXAN® and a BCMA antibody, result in a depletion (in some embodiments a synergistic depletion) and/or neutralization of B cells levels compared to the level of reduction with RITUXAN® and BCMA antagonists alone at many time points.

While the present invention has been described with reference to the specific embodiments thereof, it is to be understood by those skilled in the art that various changes may be made and an equivalence may be substituted without departing from the true spirit and scope of the invention. In addition, many modifications may be made to adapt a particular situation, material, composition of matter, process, process step or steps, to the object, spirit and scope of the present invention. All such modifications are intended to be within the scope of the claims appended hereto.

That which is claimed:

1. A method of reducing the systemic lupus erythematosus (SLE) disease activity of an individual clinically diagnosed with SLE, said method comprising:
  analyzing peripheral blood B cells from an individual clinically diagnosed with SLE for the presence or absence of elevated BCMA protein expression levels on said peripheral blood B cells, said analyzing step comprising:
   (i) measuring a first level of BCMA protein expression on the surface of peripheral blood B cells from said individual clinically diagnosed with SLE;
   (ii) comparing the first level to a second level of BCMA protein expression on the surface of peripheral blood B cells from a healthy individual; and
   (iii) identifying an individual wherein the first level is elevated as compared to the second level; and
  administering a BLyS antagonist to said individual clinically diagnosed with SLE and having elevated BCMA protein expression levels on said peripheral blood B cells, wherein the BLyS antagonist is a receptor extracellular domain/Fc domain fusion protein selected from the group consisting of TACI-Ig, BCMA-Ig, and BAFF-R-Ig,
  wherein the SLE disease activity of said individual is reduced following said administration of the BLyS antagonist.

2. The method of claim 1 wherein said BLyS antagonist is also an APRIL antagonist.

3. The method of claim 1, wherein said receptor-extracellular domain/Fc domain fusion protein is TACI-Ig.

4. The method of claim 3, wherein said TACI-Ig is atacicept.

* * * * *